US008227411B2

(12) United States Patent
Zamora et al.

(10) Patent No.: US 8,227,411 B2
(45) Date of Patent: Jul. 24, 2012

(54) FGF GROWTH FACTOR ANALOGS

(75) Inventors: Paul O. Zamora, Gaithersburg, MD (US); Louis A. Pena, Poquott, NY (US); Xinhua Lin, Plainview, NY (US); Kazuyuki Takahashi, Germantown, MD (US)

(73) Assignees: BioSurface Engineering Technologies, Incle, Rockvile, MD (US); Brookhaven and Science Associates, Upton, NY (US)

( * ) Notice: Subject to any disclaimer, the term of this patent is extended or adjusted under 35 U.S.C. 154(b) by 143 days.

(21) Appl. No.: 11/361,565

(22) Filed: Feb. 23, 2006

(65) Prior Publication Data
US 2006/0199764 A1 Sep. 7, 2006

Related U.S. Application Data

(63) Continuation-in-part of application No. 11/064,039, filed on Feb. 22, 2005, now Pat. No. 7,482,427, and a continuation-in-part of application No. 10/644,703, filed on Aug. 19, 2003, now Pat. No. 7,700,563, which is a continuation-in-part of application No. 10/224,268, filed on Aug. 20, 2002, now Pat. No. 7,166,574, application No. 11/361,565, which is a continuation-in-part of application No. 11/065,970, filed on Feb. 24, 2005, now Pat. No. 7,598,224.

(60) Provisional application No. 60/656,860, filed on Feb. 25, 2005, provisional application No. 60/547,012, filed on Feb. 20, 2004, provisional application No. 60/547,626, filed on Feb. 24, 2004.

(51) Int. Cl.
*A61K 38/18* (2006.01)
*C07K 14/50* (2006.01)
*C07K 1/00* (2006.01)

(52) U.S. Cl. .......... 514/9.1; 530/399; 530/350; 530/402
(58) Field of Classification Search ........................ None
See application file for complete search history.

(56) References Cited

U.S. PATENT DOCUMENTS

| 3,272,204 | A | 9/1966 | Artandi et al. |
| 4,172,128 | A | 10/1979 | Thiele et al. |
| 4,193,138 | A | 3/1980 | Okita |
| 4,563,350 | A | 1/1986 | Nathan et al. |
| 4,747,848 | A | 5/1988 | Maini |
| 4,842,575 | A | 6/1989 | Hoffman, Jr. et al. |
| 5,108,436 | A | 4/1992 | Chu et al. |
| 5,197,977 | A | 3/1993 | Hoffman, Jr. et al. |
| 5,202,311 | A | 4/1993 | Folkman et al. |
| 5,326,695 | A | 7/1994 | Andersson et al. |
| 5,509,899 | A | 4/1996 | Fan et al. |
| 5,510,418 | A | 4/1996 | Rhee et al. |
| 5,512,545 | A | 4/1996 | Brown et al. |
| 5,563,046 | A | 10/1996 | Mascarenhas et al. |
| 5,608,035 | A | 3/1997 | Yanofsky et al. |
| 5,635,597 | A | 6/1997 | Barrett et al. |
| 5,643,873 | A | 7/1997 | Barrett et al. |
| 5,648,458 | A | 7/1997 | Cwirla et al. |
| 5,650,234 | A | 7/1997 | Dolence et al. |
| 5,654,276 | A | 8/1997 | Barrett et al. |
| 5,665,114 | A | 9/1997 | Weadock et al. |
| 5,668,110 | A | 9/1997 | Barrett et al. |
| 5,674,977 | A | 10/1997 | Gariepy |
| 5,679,637 | A | 10/1997 | Lappi et al. |
| 5,679,673 | A | 10/1997 | Bowen et al. |
| 5,684,136 | A | 11/1997 | Godowski |
| 5,728,802 | A | 3/1998 | Barrett et al. |
| 5,759,515 | A | 6/1998 | Rhodes et al. |
| 5,767,234 | A | 6/1998 | Yanofsky et al. |
| 5,770,704 | A | 6/1998 | Godowski |
| 5,773,569 | A | 6/1998 | Wrighton et al. |
| 5,786,322 | A | 7/1998 | Barrett et al. |
| 5,786,331 | A | 7/1998 | Barrett et al. |
| 5,789,182 | A | 8/1998 | Yayon et al. |

(Continued)

FOREIGN PATENT DOCUMENTS

| WO | WO00/18921 | 4/2000 |
| WO | WO0064481 | 11/2000 |
| WO | WO0204015 | 1/2002 |
| WO | WO0210221 | 2/2002 |
| WO | WO-02/20033 | 3/2002 |
| WO | WO0219963 | 3/2002 |
| WO | WO-02/062823 | 8/2002 |

OTHER PUBLICATIONS

Baird et al. Receptor-and heparin-binding domains of basic fibroblast growth factor. Proc. Natl. Acad. Sci. vol. 85, pp. 2324-2328 (Apr. 1988).*

(Continued)

*Primary Examiner* — Elizabeth C Kemmerer
*Assistant Examiner* — Regina M Deberry
(74) *Attorney, Agent, or Firm* — Peacock Myers, P.C.; Janeen Vilven

(57) ABSTRACT

The present invention provides a fibroblast growth factor heparin-binding analog of the formula:

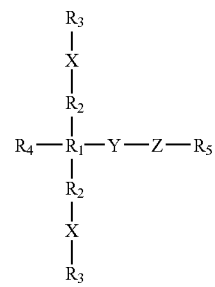

where $R_1$, $R_2$, $R_3$, $R_4$, $R_5$, X, Y and Z are as defined, pharmaceutical compositions, coating compositions and medical devices including the fibroblast growth factor heparin-binding analog of the foregoing formula, and methods and uses thereof.

10 Claims, 12 Drawing Sheets

U.S. PATENT DOCUMENTS

| | | |
|---|---|---|
| 5,830,851 A | 11/1998 | Wrighton et al. |
| 5,830,995 A | 11/1998 | Shoyab et al. |
| 5,854,207 A | 12/1998 | Lee et al. |
| 5,861,476 A | 1/1999 | Barrett et al. |
| 5,866,113 A | 2/1999 | Hendriks et al. |
| 5,869,451 A | 2/1999 | Dower et al. |
| 5,880,096 A | 3/1999 | Barrett et al. |
| 5,902,799 A | 5/1999 | Herrmann et al. |
| 5,916,585 A | 6/1999 | Cook et al. |
| 5,932,462 A | 8/1999 | Harris et al. |
| 5,945,457 A | 8/1999 | Plate et al. |
| 5,952,474 A | 9/1999 | Kayman et al. |
| 5,955,588 A | 9/1999 | Tsang et al. |
| 5,965,532 A | 10/1999 | Bachovchin |
| 5,989,866 A | 11/1999 | Deisher et al. |
| 5,994,104 A | 11/1999 | Anderson et al. |
| 6,001,364 A | 12/1999 | Rose et al. |
| 6,011,002 A | 1/2000 | Pastan et al. |
| 6,030,812 A | 2/2000 | Bauer et al. |
| 6,051,648 A | 4/2000 | Rhee et al. |
| 6,096,798 A | 8/2000 | Luthra et al. |
| 6,099,562 A | 8/2000 | Ding et al. |
| 6,102,932 A | 8/2000 | Kurz |
| 6,113,629 A | 9/2000 | Ken |
| 6,120,904 A | 9/2000 | Hostettler et al. |
| 6,121,236 A | 9/2000 | Ben-Sasson |
| 6,136,015 A | 10/2000 | Kurz et al. |
| 6,159,165 A | 12/2000 | Ferrera et al. |
| 6,165,194 A | 12/2000 | Denardo |
| 6,168,615 B1 | 1/2001 | Ken et al. |
| 6,168,784 B1 | 1/2001 | Offord et al. |
| 6,171,326 B1 | 1/2001 | Ferrera et al. |
| 6,174,530 B1 | 1/2001 | Rose et al. |
| 6,174,721 B1 | 1/2001 | Innis |
| 6,214,795 B1 | 4/2001 | Benjamin et al. |
| 6,217,873 B1 | 4/2001 | Rose et al. |
| 6,221,066 B1 | 4/2001 | Ferrera et al. |
| 6,231,600 B1 | 5/2001 | Zhong |
| 6,231,892 B1 | 5/2001 | Hubbell et al. |
| 6,235,716 B1 | 5/2001 | Ben-Sasson |
| 6,248,057 B1 | 6/2001 | Mavity et al. |
| 6,251,864 B1 | 6/2001 | Dower et al. |
| 6,258,371 B1 | 7/2001 | Koulik et al. |
| 6,270,788 B1 | 8/2001 | Koulik et al. |
| 6,284,503 B1 | 9/2001 | Caldwell et al. |
| 6,294,359 B1 | 9/2001 | Fiddes et al. |
| 6,306,153 B1 | 10/2001 | Kurz et al. |
| 6,306,165 B1 | 10/2001 | Patnaik et al. |
| 6,309,660 B1 | 10/2001 | Hsu et al. |
| 6,323,323 B1 | 11/2001 | Sledziewski et al. |
| 6,326,468 B1 | 12/2001 | Canne et al. |
| 6,342,591 B1 | 1/2002 | Zamora et al. |
| 6,350,731 B1 | 2/2002 | Jehanli et al. |
| 6,368,347 B1 | 4/2002 | Maini et al. |
| 6,377,349 B1 | 4/2002 | Fercher |
| 6,383,204 B1 | 5/2002 | Ferrera et al. |
| 6,387,978 B2 | 5/2002 | Ronan et al. |
| 6,406,687 B1 | 6/2002 | Luthra et al. |
| 6,410,044 B1 | 6/2002 | Chudzik et al. |
| 6,416,541 B2 | 7/2002 | Denardo et al. |
| 6,426,332 B1 | 7/2002 | Rueger et al. |
| 6,451,543 B1 | 9/2002 | Kochendoerfer et al. |
| 6,458,889 B1 | 10/2002 | Trollsas et al. |
| 6,491,965 B1 | 12/2002 | Berry et al. |
| 6,497,729 B1 | 12/2002 | Moussy et al. |
| 6,514,534 B1 | 2/2003 | Sawhney |
| 6,534,591 B2 | 3/2003 | Rhee et al. |
| 6,548,634 B1 | 4/2003 | Ballinger et al. |
| 6,551,305 B2 | 4/2003 | Ferrera et al. |
| 6,585,765 B1 | 7/2003 | Hossainy et al. |
| 6,596,699 B2 | 7/2003 | Zamora et al. |
| 6,616,617 B1 | 9/2003 | Ferrera et al. |
| 6,630,580 B2 | 10/2003 | Tsang et al. |
| 6,638,291 B1 | 10/2003 | Ferrera et al. |
| 6,656,201 B2 | 12/2003 | Ferrera et al. |
| 6,656,218 B1 | 12/2003 | Denardo et al. |
| 6,818,018 B1 | 11/2004 | Sawhney |
| 6,846,853 B2 | 1/2005 | Shimp |
| 6,863,899 B2 | 3/2005 | Koblish et al. |
| 6,866,155 B2 | 3/2005 | Nagel |
| 6,921,811 B2 | 7/2005 | Zamora et al. |
| 6,949,251 B2 | 9/2005 | Dalal et al. |
| 6,984,393 B2 | 1/2006 | Amsden |
| 7,025,990 B2 | 4/2006 | Sawhney |
| 7,041,641 B2 | 5/2006 | Rueger et al. |
| 7,166,574 B2 | 1/2007 | Pena et al. |
| 7,241,736 B2 | 7/2007 | Hunter et al. |
| 7,414,028 B1 | 8/2008 | Zamora et al. |
| 7,468,210 B1 | 12/2008 | Zamora |
| 7,482,427 B2 | 1/2009 | Pena et al. |
| 7,528,105 B1 | 5/2009 | Pena et al. |
| 7,598,224 B2 | 10/2009 | Zamora et al. |
| 7,671,012 B2 | 3/2010 | Zamora et al. |
| 7,700,563 B2 | 4/2010 | Pena et al. |
| 2001/0014662 A1 | 8/2001 | Rueger et al. |
| 2002/0115836 A1 | 8/2002 | Tsang et al. |
| 2002/0160098 A1 | 10/2002 | Zamora et al. |
| 2003/0224996 A1 | 12/2003 | Opperman et al. |
| 2004/0038348 A1 | 2/2004 | Pena et al. |
| 2004/0068266 A1 | 4/2004 | Delmotte |
| 2004/0087505 A1 | 5/2004 | Pena et al. |
| 2004/0151764 A1 | 8/2004 | Zamora |
| 2005/0196425 A1 | 9/2005 | Zamora |
| 2005/0222394 A1 | 10/2005 | Zamora et al. |
| 2006/0024347 A1 | 2/2006 | Zamora et al. |
| 2006/0205652 A1 | 9/2006 | Zamora et al. |
| 2008/0063622 A1 | 3/2008 | Zamora et al. |
| 2008/0160169 A1 | 7/2008 | Zamora et al. |
| 2008/0166392 A1 | 7/2008 | Zamora et al. |
| 2008/0227696 A1 | 9/2008 | Takahashi et al. |
| 2009/0111743 A1 | 4/2009 | Takahashi |
| 2009/0143566 A1 | 6/2009 | Zamora et al. |

OTHER PUBLICATIONS

Ahmed, Asif et al., "Role of VEFGF Receptor-1 (Fit-1) in Mediating Calcium-Dependent Nitric Oxide Release and Limiting DNA Synthesis in Human Trophoblast Cells", *Lab Invet*, vol. 76(6) 1997, 779-791.

Binetruy-Tournaire, Roselyne et al., "Identification of a peptide blocking vascular endothelial growth factor (VEGF)-mediated angiogenesis", *The EMBO Journal*, vol. 19 2000, 1525-1533.

Brennand, David M. et al., "Identification of a Cyclic Peptide Inhibitor of Platelet-Derived Growth Factor-BB Receptor-Binding and Mitogen-Induced DNA Synthesis in Human Fibroblasts", *FEBS Letters*, 413 1997, 70-74.

Engstrom, Ulla et al., "Identification of a Peptide Antagonist for Platelet-Derived Growth Factor", *The Journal of Biological Chemistry*, vol. 273, No. 25 1998, 15811-15817.

Gay, Cyril G. et al., "Interleukin 1 regulated heparin-binding growth factor 2 gene expression in vascular smooth muscle cells", *Proc. Natl. Acad. Sci. USA*, vol. 88 Jan. 1991, 296-300.

Ostman, Arne et al., "Identification of Three Amino Acids in the Platelet-Derived Growth Factor (PDGF) B-chain that are Important for Binding to the PDGF B-Receptor", *The Journal of Biological Chemistry*, vol. 266, No. 16, Issue of Jun. 5, 1991, 10073-10077.

Pellegrini, Luca et al., "Role of heparan sulfate in fibroblast growth factor signaling a structural view", *Structural Biology* 2001, 629-634.

Smith, Temple F. et al., "The challenges of genome sequence annotation of 'The devil is in the details'", *Nature Biotechnology*, vol. 15 Nov. 1997, 1222-1223.

Wells, James A. et al., "Additivity of Mutational Effects in Proteins", *American Chemical Society*, vol. 29, No. 37 Sep. 18, 1990, 8509-8516.

Yoneda, Atsuko et al., "Engineering of an FGF-proteoglycan fusion protein with heparin-independent, mitogenic activity", *Nature Biotechnology vol. 18* Jun. 2000, 641-644.

Kirsch, Thomas et al., "BMP-2 Antagonists Emerge from Alterations in the Low-Affinity Binding Epitope for Receptor BMPR-II", *EMBO Journal*, vol. 19, No. 13 2000, 3314-3324.

Andrades, Jose A. et al., "A Recombinant Human TGF-B1 Fusion Protein with Collagen-Binding Domain Promostes Migration, Growth, and Differentiation of Bone Marrow Mesenchymal Cells", *Experimental Cell Research vol. 250.* 1999, 485-498.

Ballinger, Marcus D. et al., "Semirational design of a potent, artificial agonist of fibroblast growth factor receptors", *Nature Biotechnology vol. 17* 1999, 1199-1204.

Bork, Peer, "Go Hunting in Sequence Databases But Watch Out for Traps", *TIG Vo. 12 No. 10* Oct. 1996, 425-427.

Bork, Peer, "Powers and Pitfalls in Sequence Analysis: the 70% Hurdle", *Genome Research vol. 10* 2000, 398-400.

Brenner, Steve, "Errors in Genome Annotation", *Trends in Genetics vol. 15 No. 4* Apr. 1999, 132-133.

Carmeliet, Peter et al., "Growing Better Blood Vessels", *Nature Biotechnology vol. 19* 2001, 1019-1020.

Dawson, Philip E. et al., "Synthesis of Native Proteins by Chemical Ligation", *Annu. Rev. Biochem. vol. 69* 2000, 923-60.

Dikov, Michael M. et al., "A Functional Fibroblast Growth Factor-1 Immunoglulin Fusion Protein", *The Journal of Biological Chemistry*, vol. 273, No. 25 Jun. 19, 1998, 15811-15817.

Doerks, Tobias, "Protein annotation: detective work for function prediction", *Trends in Genetics vol. 14 No. 6* Jun. 1998, 248-250.

Eom, Khee D. et al., "Tandem Ligation of Multipartite Peptides with Cell-Permeable Activity", *J. Am. Chem. Soc. vol. 125* 2003, 73-83.

Feeley, Brian et al., "Influence of BMP's on the Formation of Osteoblastic Lesions in Metastatic Prostate Cancer", *Journal of Bone and Mineral Research*, vol. 20 No. 12 2005, 2189-2199.

Hasan, Maemunah et al., "IL-12 is a Heparin-Binding Cytokine", *The Journal of Immunology vol. 162* 1999, 1064-1070.

Healy, Kevin et al., "Designing biomaterials to direct biological responses", *Ann N Y Acad Sci. 875* 1999, 24-35.

Hoke, David E. et al., "A Heparin Binding Synthetic Peptide from Human HIP/RPL29 Fails to Specifically Differentiate Between Anticoagulantly Active and Inactive Species of Heparin", *Journal of Negative Results in BioMedicine vol. 2. No. 1* 2003, 1-10.

Kloen, P. et al., "BMP signaling components are expressed in human fracture callus", *Bone 33* 2003, 362-371.

Kochendoerfer, Gerd G. et al., "Design and Chemical Synthesis of Homogeneous Polymer-Modified Erythropoiesis Protein", *Science*, vol. 299 2003, 884-887.

Konishi, Sadahiko et al., "Hydroxyapatite Granule Graft Combined with Recombinant Human bone Morphogenic Protein-2 for Solid Lumbar Fusion", *Journal of Spinal Disorders & Techniques*, vol. 15, No. 3 2002, 237-244.

Laredo, James et al., "Silyl-heparin bonding improves the patency and in vivo thromboresistance of carbon-coated polytetrafluoroethylene vascular grafts", *The Midwester Vascular Surgical Society* Sep. 2003, 1-7.

Lu, Xinjie et al., "Preferential antagonism of the interactions of the integrin alpha IIb beta 3 with immobilized glycoprotein ligans by snake-venom RGD (Arg-Gly-Asp) proteins", *Biochem J 304* 1994, 929-936.

Minamide, Akihito et al., "Evaluation of Carriers of Bone Morphogenetic Protein for Spinal Fusion", *Spine vol. 26*, No. 8 2001, 933-939.

Murnaghan, Mark et al., "Time for treating bone fracture using rhBMP-2: A randomised placebo controlled mouse fracture trial", *Journal of Orthopaedic Research 23* 2005, 625-631.

Ngo, Thomas et al., "Computational Complexity; Protein Structure Prediction, and the Levinthal Paradox", *The Protein Foling Problem and Terminary Structure Prediction*, Chapter 14 1994, 491-495.

Niikura, T. et al., "Gloval Gene Profiling in Experimental Fracture Nonunions Reveals a Down Regulation of BMP Gene Expression", *52nd Annual Meeting of the Orthopaedic Research Society*, Paper No. 1673 2006.

Paris, Francois et al., "Endothelial Apoptosis as the Primary Lesion Initiating Intestinal Radiation Damage in Mice", *Science vol. 293* 2001, 293-297.

Ray, Jasohara et al., "A 10-amino acid sequence of fibroblast growth factor 2 is sufficient for its mitogenic activity on neural progenitor cells", *Proc. Natl. Acad. Sci. USA vol. 94* 1997, 7047-7052.

Richardson, Thomas P. et al., "Polymeric system for dual growth factor delivery", *Nature Biotechnology vol. 19* 2001, 293-297.

Rusnati, Marco et al., "avB3 Integrin Mediates the Cell-adhesive Capacity and Biological Activity of Basic Fibroblast Growth Factor (FGF-2) in Cultured Endothelial Cells", *Molecular Biology of the Cell vol. 8* 1997, 2449-2461.

Saito, Atsuhiro et al., "Activation of osteo-progenitor cells by a novel synthetic peptide derived from the bone morphogenetic protein-2 knuckle epitope", *Biochimica et Biophysica Acta 1651* 2003, 60-67.

Shen, Wei-Chiang et al., "Poly(I-lysine) has different membrane transport and drug-carrier properties when complexed with heparin", *Proc Natl Acad Sci USA* Dec. 1981, 7589-93.

Skolnick, Jeffrey et al., "From genes to protein structure and function: novel applications of computational approaches in the genomic era", *TIBTECH vol. 18* Jan. 2000, 34-39.

Sood, R. et al., "MDS1/EVI1 enhances TGF-B1 signaling and strengthens its growth-inhibitory effect, but the leukemia-associated fusion protein AML1/MDS1/EVI1, product of the t(3;21), abrogates growth-inhibition in response to TGF-B1", *Leukemia vol. 13* 1999, 348-357.

Takizawa, Takuma et al., "Directly Linked Soluble IL-6 Receptor-IL-6 Fusion Protein Induces Astrocyte Differentiation from Neuroepithelial Cells Via Activation of STAT3", *Cytokine vol. 13* 2001, 272-279.

Tanaka, H. et al., "Involvement of bone morphogenic protein-2 (BMP-2) in the pathological ossification process of the spinal ligament", *Rheumatology 2001;40* May 9, 2001, 1163-1168.

Tong, Yen et al., "Peptide surface modification of poly(tetrafluoroethylene-co-hexafluoropropylene) enhances its interaction with central nervous system nuerons", *J Biomed Mater Res 42* 1998, 85-95.

Tung, Ching-Hsuan et al., "Novel branching membrane translocational peptide as gene delivery vector", *Bioorq Med Chem 10*(11) 2002, 3609-3614.

Varkey, Mathew et al., "Growth factor delivery for bone tissue repair: an update", *Expert Opin. Drug Deliver.* (2004) 1(1) 2004, 19-34.

Verrecchio, Angela, "Design of Peptides with High Affinities for Heparin and Endothelial Cell Proteoglycans", *The Journal of Biological Chemistry*, vol. 275, No. 11 Mar. 17, 2000, 7701-7707.

Yano, Akira et al., "RGD motif enhances immunogenicity and adjuvanicity of peptide antigens following intranasal immunization", *Vaccine 22*(2) 2003, 237-243.

Zamora, Paul O. et al., "Local Delivery of Basic Fibroblast Growth Factor (bFGF) Using Adsorbed Silyl-heparin, Benzyl-bis(dimethylsilylmethyl)oxycarbamoyl-heparin", *Bioconjugate Chem.* 2002 Aug. 20, 2002, 920-926.

Saito, Atsuhiro et al., "Prolonged ectopic calcification induced by BMP-2-derived synthetic peptide", *Journal of Biomedical Materials Research Part A*, vol. 70 No. 1 2004, 115-121.

Seol, Yang-Jo et al., "Enhanced osteogenic promotion around dental implants with synthetic binding motif mimicking bone morphogenetic protein (BMP)-2", *Journal of Biomedical Materials Research Part A*, vol. 77 No. 3 2006, 599-607.

Fenstermaker, Robert A. et al., "A Cationic Region of the Platelet-Derived Growth Factor (PDGF) A-Chain (Arg159-Lys160-Lys161) is Required for Receptor Binding and Mitogenic Activity of the PDGF-AA Homodimer", *J. Biol. Chem.*, vol. 268 No. 14 1993, 10482-10489.

Hsu, Hailing et al., "Tumor Necrosis Factor Receptor Family Member RANK Mediates Osteoclast Differentiation and Activation Induced by Osteoprotegerin Ligand", *Proc. Natl. Acad. Sci. vol. 96* 1999, 3540-3545.

Lin, Xinhua et al., "A Synthetic, Bioactive PDGF Mimetic with Binding to Both α-PDGF and β-PDGF Receptors", *Growth Factors vol. 25 No. 2* 2007, 87-93.

Abraham, Judith A. et al., "Heparin-Binding EGF-like Growth Factor: Characterization of Rat and Mouse cDNA Clones, Protein Domain Conservation Across Species, and Transcript Expression in Tissues", Biochem. Biophys. Res. Commun. vol. 190 Issue 1, 1993, 125-133.

Akiyama, Shuichi et al., "Constitutively Active BMP Type I Receptors Transduce BMP-2 Signals without the Ligand in C2C12 Myoblasts", Exp. Cell. Res. vol. 235 No. 2, 1997, 362-369.

Attisano, Liliana et al., "Smads as Transcriptional Co-Modulators", Curr. Opin. Cell Biol. vol. 12 No. 2, 2000, 235-243.

Burkus, J. K. et al., "Clinical and Radiographic Outcomes of Anterior Lumbar Interbody Fusion Using Recombinant Human Bone Morphogenetic Protein-2", Spine vol. 27, No. 21, 2002, 2396-2408.

Burt, David W., "Evolutionary Grouping of the Transforming Growth Factor-Beta Superfamily", Biochem. Biophys. Res. Commun. vol. 184 Issue 2, 1992, 590-595.

Busch, Stephen J. et al., "Trans-Repressor Activity of Nuclear Glycosaminoglycans on Fos and Jun/AP-1 Oncoprotein-Mediated Transcription", J. Cell. Biol. vol. 116, 1992, 31-42.

Courty, Jose et al., "Mitogenic Properties of a New Endothelial Cell Growth Factor Related to Pleiotrophin", Biochem. Biophys. Res. Commun. vol. 180 Issue 1, 1991, 145-151.

Gilboa, Lilach et al., "Bone Morphogenetic Protein Receptor Complexes on the Surface of Live Cells: A New Oligomerization Mode for Serine/Threonine Kinase Receptors", Mol. Biol. Cell vol. 11 No. 3, 2000, 1023-1035.

Hampton, Brian S. et al., "Structural and Functional Characterization of full-length Heparin-Binding Growth Associated Molecule", Mol. Biol. Cell. vol. 3 Issue 1, 1992, 85-93.

Hanada, Keigo et al., "Stimulatory Effects of Basic Fibroblast Growth Factor and Bone Morphogenetic Protein-2 on Osteogenic Differentiation of Rat Bone Marrow-Derived Mesenchymal Stem Cells", J. Bone Miner Res. vol. 12 No. 10, 1997, 1606-1614.

Higashiyama, Shigeki et al., "A Heparin-Binding Growth Factor Secreted by Macrophage Like Cells that is Related to EGF", Science vol. 251 No. 4996, 1991, 936-939.

Hoodless, Pamela A. et al., "MADR1, a MAD-Related Protein That Functions in BMP2 Signaling Pathways", Cell vol. 85 No. 4, 1996, 489-500.

Hsu, David R. et al., "The Xenopus Dorsalizing Factor Gremlin Identifies a Novel Family of Secreted Proteins that Antagonize BMP Activities", Mol. Cell vol. 1 No. 5, 1998, 673-683.

Huber, Daniel et al., "Amino-Terminal Sequences of a Novel Heparin-Binding Protein with Mitogenic Activity for Endothelial Cells from Human Bovine, Rat, and Chick Brain: High Interspecies Homology", Neurochem. Res. vol. 15, 1990, 435-439.

Iwasaki, Shoji et al., "Specific Activation of the p38 Mitogen-activated Protein Kinase Signaling Pathway and Induction of Neurite Outgrowth in PC12 Cells by Bone Morphogenetic Protein-2", J. Biol. Chem. vol. 274 No. 37, 1999, 26503-26510.

Katsuura, Mieko et al., "The NH2-terminal region of the active domain of sonic hedgehog is necessary for its signal transduction", FEBS Lett. vol. 447 No. 2-3, 1999.

Kawabata, Masahiro, "Cloning of a Novel Type II Serine/Threonine Kinase Receptor through Interaction with the Type I Transforming Growth Factor-βReceptor", J. Biol. Chem. vol. 270 No. 10, 1995, 5625-5630.

Kinto, Naoki et al., "Fibroblasts expressing Sonic hedgehog induce osteoblast differentiation and ectopic bone formation", FEBS Lett. vol. 404 No. 2-3, 1997, 319-323.

Kleeman, Thomas J. et al., "Laparoscopic Anterior Lumbar Interbody Fusion With rhBMP-2: A Prospective Study of Clinical and Radiographic Outcomes", Spine vol. 26, No. 24, 2001, 2751-2756.

Kuo, Ming-Der, "Characterization of Heparin-Binding Growth-Associated Factor Receptor in NIH 3T3 Cells", Biochem. Biophys. Res. Commun. vol. 182 Issue 1, 1992, 188-194.

Lin, Xinhua et al., "Augmentation of Deminerlized Bone Matrix by a Synthetic FGF-2 Mimetic", Journal of Bone and Mineral Research vol. 20, No. 9, Suppl. 1, 2005, S344-S345.

Marikovsky, Moshe et al., "Appearance of Heparin-Binding EGF-like Growth Factor in Wound Fluid as a Response to Injury", Proc. Natl. Acad. Sci. (USA) vol. 90 No. 9, 1993, 3889-3893.

Massague, Joan et al., "Controlling TGF-βsignaling", Genes Dev. vol. 14 No. 6, 2000, 627-644.

McKay, Bill et al., "Summary Statement: Overview of Bone Morphogenetic Proteins for Spine Fusion", Spine vol. 27, No. 16, Suppl 1, 2002, S66-85.

Miyazono, Kohei, "Positive and negative regulation of TGF-beta signaling", J. Cell Sci. vol. 113 Part 7, 2000, 1101-1109.

Morone, Michael A. et al., "The Marshall R. Urist Young Investigator Award. Gene expression during autograft lumbar spine fusion and the effect of bone morphogenetic protein 2", Clin. Orthop. vol. 351, 1998, 252-265.

Nakamura, Takahashi et al., "Induction of Osteogenic Differentiation by Hedgehog Proteins", Biochem. Biophys. Res. Comm. vol. 237 No. 2, 1997, 465-469.

Nohe, Anja et al., "The Mode of Bone Morphogenetic Protein (BMP) Receptor Oligomerization Determines Different BMP-2 Signaling Pathways", J. Biol. Chem. vol. 277 No. 7, 2002, 5330-5338.

Nohno, Tsutomo et al., "Identification of a Human Type II Receptor for Bone Morphogenetic Protein-4 That Forms Differential Heteromeric Complexes with Bone Morphogenetic Protein Type I Receptors", J. Biol. Chem. vol. 270 No. 38, 22522-22526, 1995.

Poynton, Ashley R. et al., "Safety Profile for the Clinical Use of Bone Morphogenetic Proteins in the Spine", Spine vol. 27, No. 16, Suppl. 1, 2002, S40-48.

Reddi, A. H., "Bone Morphogenetic Proteins: From Basic Science to Clinical Applications", J. Bone Joint Surg. AM, vol. 83-8 Suppl. 1 Pt. 1, 2001, S1-S6.

Rosenzweig, Bradley et al., "Cloning and characterization of a human type II receptor for bone morphogenetic proteins", Proc. Natl. Acad. Sci. USA, vol. 92 No. 17, 1995, 7632-7636.

Spinella-Jaegle, Sylviane et al., "Sonic hedgehog increases the commitment of pluripotent mesenchymal cells into the osteoblastic lineage and abolishes adipocytic differentiation", J. Cell Sci. vol. 114 Part 11, 2001, 2085-209.

Suzuki, Yoshihisa et al., "Alginate hydrogel linked with synthetic oligopeptide derived from BMP-2 allows ectopic osteoinduction in vivo", J. Biomed. Mater. Res. vol. 50 No. 3, 2000, 405-409.

Wang, Jian-Sheng, "Basic fibroblast growth factor and bone induction in rats", Acta. Orthop. Scand. vol. 64 No. 5, 1993, 557-561.

White, Kyle K. et al., "Mineralization of substrates modified with BMP-7 derived peptides", American Society of Mechanical Engineers BED-vol. 50, 2001, 201-202.

Wozney, John M., "Overview of Bone Morphogenetic Proteins", Spine vol. 27, No. 16, Suppl 1, 2002, S2-S8.

Yuasa, Takahito, "Sonic hedgehog is involved in osteoblast differentiation by cooperating with BMP-2", J. Cell Physiol. vol. 193 No. 2, 2002, 225-232.

Zimmerman, Lyle B. et al., "The Spemann Organizer Signal noggin Binds and Inactivates Bone Morphogenetic Protein 4", Cell vol. 86 No. 4, 1996, 599-606.

Aaronson, Stuart A. et al., "Human KGF is FGF-related with Properties of a Paracrine Effector of Epithelial Cell Growth", Science vol. 245 No. 4919, 1989, 752-755.

Aaronson, Stuart A. et al., "Keratinocyte Growth Factor. A Fibroblast Growth Factor Family Member with Unusual Target Cell Specificity", Annals NY Acad. Sci. vol. 638, 1991, 62-77.

Bates, Brian et al., "Biosynthesis of Human Fibroblast Growth Factor 5", Mol. Cell Biol., vol. 11 No. 4, 1991, 1840-1845.

Blunt, Allison G. et al., "Overlapping Expression and Redundant Activation of Mesenchymal Fibroblast Growth Factor (FGF) Receptors by Alternatively Spliced FGF-8 Ligands", J. Biol. Chem. vol. 272 No. 6, 1997, 3733-3738.

Burgess, Wilson H. et al., "The Heparin-Binding (Fibroblast) Growth Factor Family of Proteins", Ann. Rev. Biochem. vol. 58, 1989, 575-606.

Dubrulle, Julien et al., "FGF Signaling Controls Somite Boundary Position and Regulates Segmentation Clock Control of Spatiotemporal Hox Gene Activation", Cell vol. 106 Issue 2, 2001, 219-232.

Fekete, Donna, "Ear rings: FGF3 involvement comes full circle", Trends in Neurosci., vol. 23 No. 8, 2000, 332.

Fox, John E., "Multiple Peptide Synthesis", Mol. Biotechnol., vol. 3 No. 3, 1995, 249-258.

Gemel, Joanna, "Structure and Sequence of Human FGF8", Genomics vol. 35 Issue 1, 1996, 253-257.

Greene, J. M. et al., "Identification and Characterization of a Novel Member of the Fibroblast Growth Factor Family", Eur J. Neurosci vol. 10, No. 5, 1998, 1911-1925.

Hoshikawa, Masamitsu et al., "Structure and Expression of a Novel Fibroblast Growth Factor, FGF-17, Preferentially Expressed in the Embryonic Brain", Biochem. Biophys. Res. Commun. vol. 244 No. 1, 1998, 187-191.

Hu, Mickey C. et al., "FGF-18, a Novel Member of the Fibroblast Growth Factor Family, Stimulates Hepatic and Intestinal Proliferation", Mol. Cell Biol. vol. 18 No. 10, 1998, 6063-6074.

Iida, Shinya et al., "Human hst-2 (FGF-6) Oncogene: cDNA Cloning and Characterization", Oncogene vol. 7 No. 2, 1992, 303-309.

Jeffers, Michael et al., "Identification of a Novel Human Fibroblast Growth Factor and Characterization of its Role in Oncogenesis", Cancer Res. vol. 61, No. 7, 2001, 3131-3138.

Kok, L. D. S. et al., "Cloning and Characterization of a cDNA Encoding a Novel Fibroblast Growth Factor Preferentially Expressed in Human Heart", Biochem. Biophys. Res. Comm. vol. 255 No. 3, 1999, 717-721.

Lin, Xinhua et al., "Augmentation of Osseous Phenotypes in Vivo with a Synthetic Peptide", Journal of Orthopaedic Research, 2007, 531-539.

Lin, Xinhua , "Multidomain Synthetic Peptide B2A2 Synergistically Enhances BMP-2 in Vitro", Journal of Bone and Mineral Research vol. 20, No. 4, 2005, 693-703.

Lin, Xinhua et al., "Synthetic Peptide F2A4-K-NS. Mimics Fibroblast Growth Factor-2 in Vitro and is Angiogenic in Vivo", International Journal of Molecular Medicine vol. 17, No. 5, 2006, 833-839.

Marchese, C. et al., "Human Keratinocyte Growth Factor Activity on Proliferation and Differentiation of Human Keratinocytes: Differentiation Reponse Distinguishes KGF from EGF Family", J. Cellular Physiol. vol. 144 Issue 2, 1990, 326-332.

Marics, Irene et al., "Characterization of the HST-Related FGF-6 Gene, a New Member of the Fibroblast Factor Gene Family", Oncogene vol. 4 No. 3, 1989, 335-340.

McWhirter, John R. et al., "A Novel Fibroblast Growth Factor Gene Expressed in the Developing Nervous System is a Downstream Target of the Chimeric Homeodomain Oncoprotein E2A-Pbx1", Development vol. 124 No. 17, 1997, 3221-3232.

Merrifield, Bruce , "Concept and Early Development of Solid-Phase Peptide Synthesis", Methods in Enzymol, vol. 289, 1997, 3-13.

Miyake, Ayumi et al., "Structure and Expression of a Novel Member, FGF-16, of the Fibroblast Growth Factor Family", Biochem. Biophys. Res. Commun. vol. 243 No. 1, 1998, 148-152.

Miyamoto, Masaaki et al., "Molecular Cloning of a Novel Cytokine cDNA Encoding the Ninth Member of the Fibroblast Growth Factor Family, Which has a Unique Secretion Pattern", Mol. Cell. Biol. vol. 13 No. 7, 1993, 4251-4259.

Nakatake, Yuhki et al., "Identification of a Novel Fibroblast Growth Factor, FGF-22, Preferentially Expressed in the Inner Root Sheath of the Hair Follicle", Biochim. Biophys. Acta. vol. 1517 No. 3, 2001, 460-463.

Naruo, Ken-Ichi et al., "Novel Secretory Heparin-Binding Factors from Human Glioma Cells (Glia-Activating Factors) Involved in Glial Cell Growth", J. Biol. Chem. vol. 268 No. 4, 1993, 2857-2864.

Nishimura, Tetsuya et al., "dentification of a Novel FGF, FGF-21, Preferentially Expressed in the Liver", Biochim. Biophys. Acta. vol. 1492 No. 1, 2000, 203-206.

Nyfeler, Rolf , "Peptide Synthesis via Fragment Condensation", Methods Mol. Biol., vol. 35, 1994, 303-316.

Ohbayashi, Norihiko et al., "Structure and Expression of the mRNA Encoding a Novel Fibroblast Growth Factor, FGF-18", J. Biol. Chem. vol. 273 No. 29, 1998, 18161-18164.

Ohmachi, Shigeki et al., "FGF-20, a Novel Neurotrophic Factor, Preferentially Expressed in the Substantia Nigra Pars Compacta of Rat Brain", Biochem. Biophys. Res. Commun. vol. 277 No. 2, 2000, 355-360.

Sakamoto, Hiromi et al., "Adenovirus-mediated transfer of the HST-1 (FGF4) gene induces increased levels of platelet count in vivo", Proc. Natl. Acad. Sci. USA, vol. 91 No. 26, 1994, 12368-12372.

Shimada, Takahashi et al., "Cloning and Characterization of FGF23 as a Causative Factor of Tumor-Induced Osteomalacia", Proc. Natl. Acad. Sci. (USA) vol. 98 No. 11, 2001, 6500-6505.

Sidhu, Sachdev , "Phage Display for Selection of Novel Binding Peptides", Methods Enzymol, vol. 328, 2000, 333-363.

Tanaka, Shinji et al., "A Novel Isoform of Human Fibroblast Growth Factor 8 is Induced by Androgens and Associated with Progression of Esophageal Carcinoma", Dig. Dis. Sci. vol. 46 No. 5, 2001, 1016-1021.

Wade, John D. et al., "Solid Phase Peptide Synthesis; Recent Advances and Applications", Austral. Biotechnol., vol. 3 No. 6, 1993, 332-336.

Xie, Ming-Hong et al., "FGF-19, a Novel Fibroblast Growth Factor with Unique Specificity for FGFR4", Cytokine vol. 11 No. 10, 1999, 729-735.

Xu, Jingsong et al., "Genomic Structure, Mapping, Activity and Expression of Fibroblast Growth Factor 17", Mechanisms of Development vol. 83, 1999, 165-178.

Yamashita, Tetsuo et al., "Identification of a Novel Fibroblast Growth Factor, FGF-23, Preferentially Expressed in the Ventrolateral Thalamic Nucleus of the Brain", Biochem. Biophys. Res. Commun. vol. 277 No. 2, 2000, 494-498.

Zhan, Xi et al., "The Human FGF-5 Oncogene Encodes a Novel Protein Related to Fibroblast Growth Factors", Mol. Cell Biol. vol. 8 No. 8, 1988, 3487-3495.

* cited by examiner

NH₂-K-K-Hex-Hex-Hex-RKRKLERIAR-amide

```
     N  N  ⎫
     R  R  ⎬  spacer      Heparin
     F  F  ⎭              Binding
     H  H                 Domain
     S  S
     W  W
     D  D
     CC
     I  I
     K  K
     T  T
     W  W
     A  A
     S  S         Receptor
     D  D    ⎫    Binding
     T  T    ⎬    Domain
     F  F    ⎭
     V  V
     L  L
     V  V
     CC
     Y  Y
     D  D
     D  D
     G  G
     S  S
     E  E
     A  A
     |  |
    NH₂ NH₂
```

FIG. 1

NH₂-K-K-Hex-Hex-Hex-RKRKLERIAR-amide

```
 | |   ⎫
 Y Y   ⎬ spacer       Heparin
 R R   ⎭               Binding
 S S                   Domain
 R R   ⎫
 K K   ⎪
 Y Y   ⎪
 S S   ⎬ Receptor
 S S   ⎪  Binding
 W W   ⎪  Domain
 Y Y   ⎪
 V V   ⎪
 A A   ⎪
 L L   ⎪
 K K   ⎪
 R R   ⎭
 | |
NH₂ NH₂
```

FIG. 2

SEQUENCE LISTING

<160> NUMBER OF SEQ ID NOS: 49

<210> SEQ ID NO 1
<211> LENGTH: 6
<212> TYPE: PRT
<213> ORGANISM: Artificial
<220> FEATURE:
<223> OTHER INFORMATION: Heparin Binding Motif
<220> FEATURE:
<221> NAME/KEY: misc_feature
<222> LOCATION: (1)..(3)
<223> OTHER INFORMATION: Lysine or Arginine
<220> FEATURE:
<221> NAME/KEY: misc_feature
<222> LOCATION: (4)..(5)
<223> OTHER INFORMATION: any naturally or non-naturally occuring amino
      acid
<220> FEATURE:
<221> NAME/KEY: misc_feature
<222> LOCATION: (6)..(6)
<223> OTHER INFORMATION: Lysine or Arginine

<400> SEQUENCE: 1

Xaa Xaa Xaa Xaa Xaa Xaa
1               5

<210> SEQ ID NO 2
<211> LENGTH: 10
<212> TYPE: PRT
<213> ORGANISM: Artificial
<220> FEATURE:
<223> OTHER INFORMATION: Heparin Binding Motif

<400> SEQUENCE: 2

Arg Lys Arg Lys Leu Glu Arg Ile Ala Arg
1               5                   10

<210> SEQ ID NO 3
<211> LENGTH: 10
<212> TYPE: PRT
<213> ORGANISM: Artificial
<220> FEATURE:
<223> OTHER INFORMATION: Heparin Binding Motif

<400> SEQUENCE: 3

Arg Lys Arg Lys Leu Gly Arg Ile Ala Arg
1               5                   10

<210> SEQ ID NO 4
<211> LENGTH: 10
<212> TYPE: PRT
<213> ORGANISM: Artificial
<220> FEATURE:
<223> OTHER INFORMATION: Heparin Binding Motif

<400> SEQUENCE: 4

Arg Lys Arg Lys Leu Trp Arg Ala Arg Ala
1               5                   10

<210> SEQ ID NO 5
<211> LENGTH: 9
<212> TYPE: PRT
<213> ORGANISM: Artificial
<220> FEATURE:
<223> OTHER INFORMATION: Heparin Binding Motif

<400> SEQUENCE: 5

Arg Lys Arg Leu Asp Arg Ile Ala Arg

```
<210> SEQ ID NO 6
<211> LENGTH: 11
<212> TYPE: PRT
<213> ORGANISM: Artificial
<220> FEATURE:
<223> OTHER INFORMATION: Heparin Binding Motif

<400> SEQUENCE: 6

Arg Lys Arg Lys Leu Glu Arg Ile Ala Arg Cys
1               5                   10

<210> SEQ ID NO 7
<211> LENGTH: 15
<212> TYPE: PRT
<213> ORGANISM: Artificial
<220> FEATURE:
<223> OTHER INFORMATION: Synthetic FGF-2 analog

<400> SEQUENCE: 7

Tyr Arg Ser Arg Lys Tyr Ser Ser Trp Tyr Val Ala Leu Lys Arg
1               5                   10                  15

<210> SEQ ID NO 8
<211> LENGTH: 28
<212> TYPE: PRT
<213> ORGANISM: Artificial
<220> FEATURE:
<223> OTHER INFORMATION: Synthetic FGF analog

<400> SEQUENCE: 8

Asn Arg Phe His Ser Trp Asp Cys Ile Lys Thr Trp Ala Ser Asp Thr
1               5                   10                  15

Phe Val Leu Val Cys Tyr Asp Asp Gly Ser Glu Ala
            20                  25

<210> SEQ ID NO 9
<211> LENGTH: 15
<212> TYPE: PRT
<213> ORGANISM: Artificial
<220> FEATURE:
<223> OTHER INFORMATION: Synthetic FGF-2 analog

<400> SEQUENCE: 9

His Ile Lys Leu Gln Leu Gln Ala Glu Glu Arg Gly Val Val Ser
1               5                   10                  15

<210> SEQ ID NO 10
<211> LENGTH: 17
<212> TYPE: PRT
<213> ORGANISM: Artificial
<220> FEATURE:
<223> OTHER INFORMATION: Synthetic FGF-1 analog

<400> SEQUENCE: 10

Tyr Ile Ser Lys Lys His Ala Glu Lys Asn Trp Phe Val Gly Leu Lys
1               5                   10                  15

Lys

<210> SEQ ID NO 11
<211> LENGTH: 15
<212> TYPE: PRT
<213> ORGANISM: Artificial
<220> FEATURE:
<223> OTHER INFORMATION: Synthetic FGF-1 analog
```

```
<400> SEQUENCE: 11

His Ile Gln Leu Gln Leu Ser Ala Glu Ser Val Gly Glu Val Tyr
1               5                   10                  15

<210> SEQ ID NO 12
<211> LENGTH: 20
<212> TYPE: PRT
<213> ORGANISM: Artificial
<220> FEATURE:
<223> OTHER INFORMATION: Synthetic FGF-7 analog

<400> SEQUENCE: 12

Tyr Ala Ser Ala Lys Trp Thr His Asn Gly Gly Glu Met Phe Val Ala
1               5                   10                  15

Leu Asn Gln Lys
            20

<210> SEQ ID NO 13
<211> LENGTH: 15
<212> TYPE: PRT
<213> ORGANISM: Artificial
<220> FEATURE:
<223> OTHER INFORMATION: Synthetic FGF-7 analog

<400> SEQUENCE: 13

Tyr Asn Ile Met Glu Ile Arg Thr Val Ala Val Gly Ile Val Ala
1               5                   10                  15

<210> SEQ ID NO 14
<211> LENGTH: 20
<212> TYPE: PRT
<213> ORGANISM: Artificial
<220> FEATURE:
<223> OTHER INFORMATION: Synthetic FGF-10 analog

<400> SEQUENCE: 14

Tyr Ala Ser Phe Asn Trp Gln His Asn Gly Arg Gln Met Tyr Val Ala
1               5                   10                  15

Leu Asn Gln Lys
            20

<210> SEQ ID NO 15
<211> LENGTH: 19
<212> TYPE: PRT
<213> ORGANISM: Artificial
<220> FEATURE:
<223> OTHER INFORMATION: Synthetic FGF-22 analog

<400> SEQUENCE: 15

Tyr Ala Ser Gln Arg Trp Arg Arg Arg Gly Gln Pro Asn Leu Ala Leu
1               5                   10                  15

Asp Arg Arg

<210> SEQ ID NO 16
<211> LENGTH: 21
<212> TYPE: PRT
<213> ORGANISM: Artificial
<220> FEATURE:
<223> OTHER INFORMATION: Synthetic FGF-9 analog

<400> SEQUENCE: 16

Tyr Ser Ser Asn Leu Tyr Lys His Val Asp Thr Gly Arg Arg Tyr Tyr
1               5                   10                  15

Val Ala Leu Asn Lys
            20
```

```
<210> SEQ ID NO 17
<211> LENGTH: 20
<212> TYPE: PRT
<213> ORGANISM: Artificial
<220> FEATURE:
<223> OTHER INFORMATION: Synthetic FGF-16 analog

<400> SEQUENCE: 17

Tyr Ala Ser Thr Leu Tyr Lys His Ser Asp Ser Glu Arg Gln Tyr Val
1               5                   10                  15

Ala Leu Asn Lys
            20

<210> SEQ ID NO 18
<211> LENGTH: 20
<212> TYPE: PRT
<213> ORGANISM: Artificial
<220> FEATURE:
<223> OTHER INFORMATION: Synthetic FGF-20 analog

<400> SEQUENCE: 18

Tyr Ser Ser Asn Ile Tyr Lys His Gly Asp Thr Gly Arg Arg Phe Val
1               5                   10                  15

Ala Leu Asn Lys
            20

<210> SEQ ID NO 19
<211> LENGTH: 16
<212> TYPE: PRT
<213> ORGANISM: Artificial
<220> FEATURE:
<223> OTHER INFORMATION: Synthetic FGF-4 analog

<400> SEQUENCE: 19

Tyr Glu Ser Tyr Lys Tyr Pro Gly Met Phe Ile Ala Leu Ser Lys Asn
1               5                   10                  15

<210> SEQ ID NO 20
<211> LENGTH: 17
<212> TYPE: PRT
<213> ORGANISM: artificial
<220> FEATURE:
<223> OTHER INFORMATION: Synthetic FGF-6 analog

<400> SEQUENCE: 20

Tyr Glu Ser Asp Leu Tyr Gln Gly Thr Tyr Ile Leu Ser Lys Tyr Gly
1               5                   10                  15

Arg

<210> SEQ ID NO 21
<211> LENGTH: 20
<212> TYPE: PRT
<213> ORGANISM: Artificial
<220> FEATURE:
<223> OTHER INFORMATION: Synthetic FGF-12 analog

<400> SEQUENCE: 21

Tyr Ser Ser Thr Leu Tyr Arg Gln Gln Glu Ser Gly Arg Ala Trp Phe
1               5                   10                  15

Leu Gly Asn Lys
            20

<210> SEQ ID NO 22
<211> LENGTH: 21
```

```
<212> TYPE: PRT
<213> ORGANISM: Artificial
<220> FEATURE:
<223> OTHER INFORMATION: Synthetic FGF-14 analog

<400> SEQUENCE: 22

Tyr Ser Ser Met Leu Tyr Arg Gln Gln Glu Ser Gly Arg Ala Trp Phe
1               5                   10                  15

Leu Gly Leu Asn Lys
            20

<210> SEQ ID NO 23
<211> LENGTH: 21
<212> TYPE: PRT
<213> ORGANISM: Artificial
<220> FEATURE:
<223> OTHER INFORMATION: Synthetic FGF-14 analog

<400> SEQUENCE: 23

Tyr Ser Ser Met Ile Tyr Arg Gln Gln Gln Ser Gly Arg Gly Trp Tyr
1               5                   10                  15

Leu Gly Leu Asn Lys
            20

<210> SEQ ID NO 24
<211> LENGTH: 19
<212> TYPE: PRT
<213> ORGANISM: Artificial
<220> FEATURE:
<223> OTHER INFORMATION: Synthetic FGF-11 analog

<400> SEQUENCE: 24

Tyr Ala Ser Ala Leu Tyr Arg Gln Arg Arg Ser Gly Arg Ala Trp Tyr
1               5                   10                  15

Leu Asp Lys

<210> SEQ ID NO 25
<211> LENGTH: 28
<212> TYPE: PRT
<213> ORGANISM: Artificial
<220> FEATURE:
<223> OTHER INFORMATION: Synthetic FGF analog

<400> SEQUENCE: 25

Ala Glu Ser Gly Asp Asp Tyr Cys Val Leu Val Phe Thr Asp Ser Ala
1               5                   10                  15

Trp Thr Lys Ile Cys Asp Trp Ser His Phe Arg Asn
            20                  25

<210> SEQ ID NO 26
<211> LENGTH: 15
<212> TYPE: PRT
<213> ORGANISM: Artificial
<220> FEATURE:
<223> OTHER INFORMATION: Synthetic FGF-2 analog

<400> SEQUENCE: 26

Arg Lys Leu Ala Val Tyr Trp Ser Ser Tyr Lys Arg Ser Arg Tyr
1               5                   10                  15

<210> SEQ ID NO 27
<211> LENGTH: 15
<212> TYPE: PRT
<213> ORGANISM: Artificial
<220> FEATURE:
<223> OTHER INFORMATION: Heparin binding domain
```

```
<220> FEATURE:
<221> NAME/KEY: misc_feature
<222> LOCATION: (3)..(3)
<223> OTHER INFORMATION: Xaa can be any naturally occurring amino acid

<400> SEQUENCE: 27

Ala His Xaa Arg Lys Arg Lys Leu Glu Arg Ile Ala Arg Asn His
1               5                   10                  15

<210> SEQ ID NO 28
<211> LENGTH: 10
<212> TYPE: PRT
<213> ORGANISM: Artificial
<220> FEATURE:
<223> OTHER INFORMATION: Synthetic FGF-1 analog

<400> SEQUENCE: 28

Ser Asn Gly Gly His Phe Leu Arg Ile Leu
1               5                   10

<210> SEQ ID NO 29
<211> LENGTH: 10
<212> TYPE: PRT
<213> ORGANISM: Artificial
<220> FEATURE:
<223> OTHER INFORMATION: Synthetic FGF-2 analog

<400> SEQUENCE: 29

Lys Asn Gly Gly Phe Phe Leu Arg Ile His
1               5                   10

<210> SEQ ID NO 30
<211> LENGTH: 9
<212> TYPE: PRT
<213> ORGANISM: Artificial
<220> FEATURE:
<223> OTHER INFORMATION: Synthetic FGF-10 analog

<400> SEQUENCE: 30

Arg Thr Gln Trp Tyr Leu Arg Ile Asp
1               5

<210> SEQ ID NO 31
<211> LENGTH: 9
<212> TYPE: PRT
<213> ORGANISM: Artificial
<220> FEATURE:
<223> OTHER INFORMATION: Synthetic FGF-10 analog

<400> SEQUENCE: 31

Phe Thr Lys Tyr Phe Leu Lys Ile Glu
1               5

<210> SEQ ID NO 32
<211> LENGTH: 9
<212> TYPE: PRT
<213> ORGANISM: Artificial
<220> FEATURE:
<223> OTHER INFORMATION: Synthetic FGF-22 analog

<400> SEQUENCE: 32

Ser Thr His Phe Phe Leu Arg Val Asp
1               5

<210> SEQ ID NO 33
<211> LENGTH: 9
<212> TYPE: PRT
<213> ORGANISM: Artificial
```

```
<220> FEATURE:
<223> OTHER INFORMATION: Synthetic FGF-9 analog

<400> SEQUENCE: 33

Arg Thr Gly Phe His Leu Glu Ile Phe
1               5

<210> SEQ ID NO 34
<211> LENGTH: 9
<212> TYPE: PRT
<213> ORGANISM: Artificial
<220> FEATURE:
<223> OTHER INFORMATION: Synthetic FGF-16 analog

<400> SEQUENCE: 34

Arg Thr Gly Phe His Leu Glu Ile Phe
1               5

<210> SEQ ID NO 35
<211> LENGTH: 9
<212> TYPE: PRT
<213> ORGANISM: Artificial
<220> FEATURE:
<223> OTHER INFORMATION: Synthetic FGF-20 analog

<400> SEQUENCE: 35

Arg Thr Gly Phe His Leu Gln Ile Leu
1               5

<210> SEQ ID NO 36
<211> LENGTH: 11
<212> TYPE: PRT
<213> ORGANISM: Artificial
<220> FEATURE:
<223> OTHER INFORMATION: Synthetic FGF-4 analog

<400> SEQUENCE: 36

Asn Val Gly Ile Gly Phe His Leu Gln Ala Leu
1               5                   10

<210> SEQ ID NO 37
<211> LENGTH: 11
<212> TYPE: PRT
<213> ORGANISM: Artificial
<220> FEATURE:
<223> OTHER INFORMATION: Synthetic FGF-7 analog

<400> SEQUENCE: 37

Asn Val Gly Ile Gly Phe His Leu Gln Val Leu
1               5                   10

<210> SEQ ID NO 38
<211> LENGTH: 9
<212> TYPE: PRT
<213> ORGANISM: Artificial
<220> FEATURE:
<223> OTHER INFORMATION: Synthetic FGF-12 analog

<400> SEQUENCE: 38

Gln Gln Gly Tyr Phe Leu Gln Met His
1               5

<210> SEQ ID NO 39
<211> LENGTH: 9
<212> TYPE: PRT
<213> ORGANISM: Artificial
<220> FEATURE:
<223> OTHER INFORMATION: Synthetic FGF-14 analog
```

```
<400> SEQUENCE: 39

Arg Gln Gly Tyr Tyr Leu Gln Met His
1               5

<210> SEQ ID NO 40
<211> LENGTH: 9
<212> TYPE: PRT
<213> ORGANISM: Artificial
<220> FEATURE:
<223> OTHER INFORMATION: Synthetic FGF-13 analog

<400> SEQUENCE: 40

Arg Gln Gly Tyr His Leu Gln Leu Gln
1               5

<210> SEQ ID NO 41
<211> LENGTH: 9
<212> TYPE: PRT
<213> ORGANISM: Artificial
<220> FEATURE:
<223> OTHER INFORMATION: Synthetic FGF-11 analog

<400> SEQUENCE: 41

Arg Gln Gly Phe Tyr Leu Gln Ala Asn
1               5

<210> SEQ ID NO 42
<211> LENGTH: 10
<212> TYPE: PRT
<213> ORGANISM: Artificial
<220> FEATURE:
<223> OTHER INFORMATION: Synthetic FGF-8 analog

<400> SEQUENCE: 42

Arg Thr Ser Gly Lys His Val Gln Val Leu
1               5                   10

<210> SEQ ID NO 43
<211> LENGTH: 10
<212> TYPE: PRT
<213> ORGANISM: Artificial
<220> FEATURE:
<223> OTHER INFORMATION: Synthetic FGF-17 analog

<400> SEQUENCE: 43

Arg Thr Ser Gly Lys His Val Gln Val Thr
1               5                   10

<210> SEQ ID NO 44
<211> LENGTH: 10
<212> TYPE: PRT
<213> ORGANISM: Artificial
<220> FEATURE:
<223> OTHER INFORMATION: Synthetic FGF-18 analog

<400> SEQUENCE: 44

Arg Thr Ser Gly Lys His Ile Gln Val Leu
1               5                   10

<210> SEQ ID NO 45
<211> LENGTH: 9
<212> TYPE: PRT
<213> ORGANISM: Artificial
<220> FEATURE:
<223> OTHER INFORMATION: Synthetic FGF-3 analog

<400> SEQUENCE: 45
```

```
Ala Thr Lys Tyr His Leu Gln Leu His
1               5

<210> SEQ ID NO 46
<211> LENGTH: 11
<212> TYPE: PRT
<213> ORGANISM: Artificial
<220> FEATURE:
<223> OTHER INFORMATION: Synthetic FGF-5 analog

<400> SEQUENCE: 46

Arg Val Gly Ile Gly Phe His Leu Gln Ile Tyr
1               5                   10

<210> SEQ ID NO 47
<211> LENGTH: 14
<212> TYPE: PRT
<213> ORGANISM: Artificial
<220> FEATURE:
<223> OTHER INFORMATION: Synthetic FGF-19 analog

<400> SEQUENCE: 47

Ser Gly Pro His Gly Leu Ser Ser Cys Phe Leu Arg Ile Arg
1               5                   10

<210> SEQ ID NO 48
<211> LENGTH: 13
<212> TYPE: PRT
<213> ORGANISM: Artificial
<220> FEATURE:
<223> OTHER INFORMATION: Synthetic FGF-21 analog

<400> SEQUENCE: 48

Asp Asp Ala Gln Gln Thr Glu Ala His Leu Glu Ile Arg
1               5                   10

<210> SEQ ID NO 49
<211> LENGTH: 12
<212> TYPE: PRT
<213> ORGANISM: Artificial
<220> FEATURE:
<223> OTHER INFORMATION: Synthetic FGF-23 analog

<400> SEQUENCE: 49

Ala Thr Ala Arg Asn Ser Tyr His Leu Gln Ile His
1               5                   10
```

FGF GROWTH FACTOR ANALOGS

CROSS-REFERENCE TO RELATED APPLICATIONS

This application claims priority to and the benefit of the filing of U.S. Provisional Patent Application Ser. No. 60/656,860, entitled "FGF Growth Factor Analogs", filed on Feb. 25, 2005 and the specification and claims thereof are incorporated herein by reference.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of Grant No. 1-R43-HL077039 awarded by the U.S. NHBLI, National Institutes of Health; Cooperative Research and Development Agreement (CRADA) between BioSurface Engineering Technologies, Inc. and Brookhaven Science Associates, LLC, operator of Brookhaven National Laboratory, No. BNL-C-03-01; and U.S. Department of Energy Contract No. DE-AC02-98CH10886.

REFERENCE TO A SEQUENCE LISTING, A TABLE, OR COMPUTER PROGRAM

This application includes a "Sequence Listing" filed herewith under 37 C.F.R. §1.821(c) on disc in accordance with 37 C.F.R. §1.821(d). Two identical copies (marked "Copy 1" and "Copy 2") of said disc, both of which contain said "Sequence Listing," are submitted herewith, for a total of two discs submitted. Said "Sequence Listing" is recorded on said discs as "FGF-Growth_US.ST25.txt" created Feb. 23, 2006, size 12.0 KB, 12,288 bytes, which is hereby incorporated by reference in this application in its entirety.

This application is a continuation-in-part of U.S. patent application Ser. No. 11/064,039, entitled Positive Modulator of Bone Morphogenic Protein-2, filed on Feb. 22, 2005, which claims the benefit of the filing of U.S. Provisional Patent Application Ser. No. 60/547,012, entitled Positive Modulator of Bone Morphogenic Protein-2, filed on Feb. 20, 2004, and is also a continuation-in-part of U.S. patent application Ser. No. 10/644,703, entitled Synthetic Heparin-Binding Growth Factor Analogs, filed on Aug. 19, 2003, which in turn is a continuation-in-part application of U.S. patent application Ser. No. 10/224,268, entitled Synthetic Heparin-Binding Growth Factor Analogs, filed on Aug. 20, 2002, and the specification thereof of each is incorporated herein by reference.

This application is a continuation-in-part of U.S. patent application Ser. No. 11/065,970 entitled Dual Chain Synthetic Heparin-Binding Growth Factor Analogs, filed on Feb. 24, 2005, which claims the benefit of the filing of U.S. Provisional Patent Application Ser. No. 60/547,626, entitled Dual Chain Synthetic Heparin-Binding Growth Factor Analogs, filed on Feb. 24, 2004, and the specification thereof of each is incorporated herein by reference.

BACKGROUND OF THE INVENTION

1. Field of the Invention (Technical Field)

The present invention relates to synthetic fibroblast growth factor (FGF) analogs, particularly analogs having at lead two sequences that bind a fibroblast growth factor receptor (FGFR), and further having a non-growth factor heparin-binding region and optionally a linker, which linker may be hydrophobic. The invention further relates to the clinical uses of such analogs as soluble drugs and as coatings for medical devices.

2. Background Art

The heparin-binding growth factors (HBGFs) constitute a large class of growth factors that includes the 23 fibroblast growth factors identified to date (FGFs 1-23). Peptides from natural HBGFs that bind heparin-binding growth factor receptors have been identified. See for example Ray et al., Proc. Natl. Acad. Sci. USA 94:7047-7052 (1997). These authors demonstrated that two amino acid sequences from FGF-2 are sufficient to block the mitogenic activity of FGF-2 on neural progenitor cells. The first peptide is a ten amino acid sequence, from amino acids 65-74, the second peptide extends from amino acids 115-129.

In an alternative approach, an artificial peptide that binds a heparin-binding growth factor receptor was identified by a phage display method. Ballinger et al., Nature BioTechnology 17:1199-1204 (1999) used this technique to isolate a 28 amino acid peptide called C19, which binds FGF-2 receptors, but by itself fails to stimulate biological activity. The peptide has no amino acid sequence identity with any known FGF.

FGF HBGFs useful in prevention or therapy of a wide range of diseases and disorders may be purified from natural sources or produced by recombinant DNA methods; however, such preparations are expensive and generally difficult to prepare.

Compositions that include homologs and analogs of fibroblast growth factors have been described. See for example U.S. Pat. No. 5,679,673 to Lappi and Baird; U.S. Pat. No. 5,989,866 to Deisher et al. and U.S. Pat. No. 6,294,359 to Fiddes et al. These disclosures relate to FGF homologs or analogs that are either conjugated to a toxic moiety and are targeted to the FGF receptor-bearing cells; or are homologs or analogs that modulate the biological pathways through the signal transduced by the FGF receptor upon binding by the FGF homolog or analog.

International Publication WO 00/18921 to Ballinger and Kavanaugh discloses a composition consisting of fusion proteins having FGF receptor affinity linked to an "oligomerization domain", either directly or through a linking group. The oligomerization domain ranges in length from about 20 to 300 residues, and includes constructs such as transcription factors, Fc portions of IgG, leucine zippers and the like. The oligomerization domains disclosed are homodimeric domains, wherein a single FGF receptor affinity fusion protein is linked to a single domain, such as a leucine zipper, which in turn is linked to a similar molecule by means of cysteine residues at both the amino and carboxy termini of the leucine zippers, such that two parallel leucine zippers, each with a single FGF receptor affinity fusion protein, are cross-linked by means of disulfide bonds. It is also disclosed that fusion proteins may include a heparin binding domain, such as the use of jun as a multimerization domain, which is asserted to be a heparin binding domain.

BRIEF SUMMARY OF THE INVENTION

One aspect of the present invention provides a fibroblast growth factor heparin-binding analog of formula I:

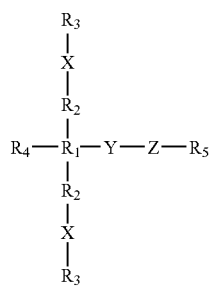

wherein:
each X is a sequence selected from SEQ ID NOs. 7-49;
$R_1$ is a single trifunctional amino acid residue covalently bonded to each X or is a dipeptide of the formula $AA_1$-$AA_2$;
$AA_1$ is an amino acid residue, wherein one of X is covalently bonded through the N-terminus of $AA_1$ or through a side chain of $AA_1$;
$AA_2$ is a trifunctional amino acid residue, wherein one of X is covalently bonded through a side chain of $AA_2$;
$R_2$ is a linker comprising a chain from 0 to about 20 backbone atoms including carbon, oxygen, nitrogen and mixtures thereof covalently bonded to $R_1$ and X;
Each $R_3$ is hydrogen (H) such that the terminal group is $NH_2$, or is an acyl group with a linear or branched $C_1$ to $C_{17}$ alkyl, aryl, heteroaryl, alkene, alkenyl or aralkyl chain including an N-terminus $NH_2$, $NH_3^+$, or NH group or a corresponding acylated derivative;
$R_4$ is not present if $R_1$ is a single trifunctional amino acid residue or if $R_1$ is a dipeptide of the formula $AA_1$-$AA_2$ wherein one of X is covalently bonded through the N-terminus of $AA_1$, and other wise is $R_3$;
$R_6$ is OH such that the terminal group is a carboxyl, $NH_2$, an acyl group with a linear or branched $C_1$ to $C_{17}$ alkyl, aryl, heteroaryl, alkene, alkenyl or aralkyl chain including an N-terminus $NH_2$, $NH_3^+$, or NH group or a corresponding acylated derivative, or NH—$R_3$;
Y is a linker comprising a chain from 0 to about 50 atoms covalently bonded to $R_1$ and Z; and
Z is a non-signaling peptide chain that includes a heparin binding domain, comprising an amino acid sequence that comprises (i) a minimum of one heparin binding motif, (ii) a maximum of about ten heparin binding motifs, and (iii) a maximum of about thirty amino acids.

Another aspect provides a heparin-binding growth factor analog of formula I, wherein X and Z are synthetic peptide chains.

Another aspect of the present invention provides a fibroblast growth factor heparin-binding analog of formula I, wherein Y can further comprise a linker that (i) is hydrophobic, (ii) comprises a chain of a minimum of about 9 and a maximum of about 50 atoms, and (iii) is not found in the natural ligand of the fibroblast growth factor receptor (FGFR).

Yet another aspect provides a fibroblast growth factor heparin-binding analog of formula I which can be characterized in that it has an avidity for heparin such that the synthetic heparin-binding growth factor analog binds heparin in 0.15 M NaCl, but is eluted by 1 M NaCl.

Still another aspect provides a fibroblast growth factor heparin-binding analog of formula I, whererin $R_1$ is a trifunctional amino acid residue, wherein one X is covalently bonded through a side chain of $R_1$ and one X is covalently bonded through the N-terminus amine of $R_1$. The $R_1$ trifunctional amino acid residue may be a diamine amino acid residue. Where $AA_2$ is provided, it may also be a diamine amino acid residue. Preferred diamine amino acid residues include a 2,3 diamino propionyl amino acid residue, a 2,4 diamino butylic amino acid residue, lysine or ornithine.)

One aspect of the present invention provides a fibroblast growth factor heparin-binding analog of formula I, wherein Y comprises between one and about thirty-three ethylene glycol units. Alternatively, Y comprises a branched or unbranched, saturated or unsaturated alkyl chain of between one and about twenty carbon atoms. Alternatively, Y comprises $[NH_2-(CH_2)_p CO]_q$ wherein p is from 1 to about 10 and q is from 1 to about 20. Alternatively, Y comprises a peptide sequence comprising from one to about 16 Gly residues.

Another aspect of the present invention provides fibroblast growth factor heparin-binding analog of formula I, wherein each heparin binding motif of Z may be of the formula BxBB or BBBxxB, wherein each B is independently lysine, arginine, ornithine, or histidine, and each x is a independently a naturally occurring amino acid. Z may comprise at least two heparin-binding motifs.

Another aspect of the present invention provides a fibroblast growth factor heparin-binding analog of claim 1, wherein $R_1$ is a single trifunctional amino acid residue, X is one of SEQ ID NO:7 through SEQ ID NO:49 and Z is one of SEQ ID NO:2 through SEQ ID NO:6.

Another aspect of the present invention provides a pharmaceutical composition comprising the fibroblast growth factor heparin-binding analog of formula I or a pharmaceutically acceptable salt thereof and a pharmaceutical carrier.

Yet another aspect of the present invention provides a coating for a medical device comprising the fibroblast growth factor heparin-binding analog of formula I or a pharmaceutically acceptable salt thereof.

Another aspect of the present invention provides a medical device comprising the fibroblast growth factor heparin-binding analog of formula I or a pharmaceutically acceptable salt thereof.

Still another aspect of the present invention provides a method to enhance wound treatment in a vertebrate animal comprising administering to a vertebrate subject in need of such treatment an effective amount of a compound that augments fibroblast growth factor activity wherein the compound is a synthetic peptide having a non-growth factor heparin binding region, a linker and a sequence that binds specifically to a fibroblast growth factor receptor. In one embodiment of the method, the compound is a fibroblast growth factor heparin-binding analog of formula I or a pharmaceutically acceptable salt thereof.

Another aspect of the present invention provides a method to stimulate growth and proliferation of cells in a vertebrate animal comprising administering to a vertebrate subject in need of such treatment an effective amount of a compound of formula I or a pharmaceutically acceptable salt thereof.

Another aspect of the present invention provides a method to stimulate angiogenesis in a vertebrate animal comprising administering to a vertebrate subject in need of such treatment an effective amount of a compound of formula I or a pharmaceutically acceptable salt thereof.

Another aspect of the present invention provides a method for treating an aneurysm in a vertebrate animal comprising introducing an embolus generating vaso-occlusive device into the aneurysm, wherein the vaso-occlusive device comprises an effective amount of a compound that augments fibroblast growth factor activity, which compound is of formula I or a pharmaceutically acceptable salt thereof.

Another aspect of the present invention provides a vaso-occlusive device, comprising an effective amount of a compound that augments fibroblast growth factor activity, which compound is of formula I or a pharmaceutically acceptable salt thereof.

Another aspect of the present invention provides a synthetic FGF analogs that include at least two peptide sequences that bind to a FGFR and a heparin-binding peptide sequence.

Another aspect of the present invention provides a synthetic FGF analogs that include at least two peptide sequences that bind to a FGFR, a heparin-binding peptide sequence and a hydrophobic spacer sequence.

Another aspect of the present invention provides a synthetic FGF analogs that may be used as coatings or components of medical devices intended for in vivo use.

Another aspect of the present invention provides a synthetic FGF analogs that may be used as pharmaceutical agents. Such pharmaceutical agents could then be delivered by standard delivery methods including.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE SEVERAL VIEWS OF THE DRAWINGS

The accompanying drawings in the attachment, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings:

FIG. 1 depicts the sequence of a synthetic FGF analog of Example 1 wherein AESGDDYCVLVFTDSAWTKICDW-SHFRN is SEQ ID NO:25 and RKRKLERIAR is SEQ ID NO:2 according to one embodiment of the present invention.

FIG. 2 depicts the sequence of a synthetic FGF analog of Example 2 wherein RKLAVYWSSYKRSRY is SEQ ID NO:26 and RKRKLERIAR is SEQ ID NO:2 according to one embodiment of the present invention.

DETAILED DESCRIPTION OF THE INVENTION

Figure 3A:
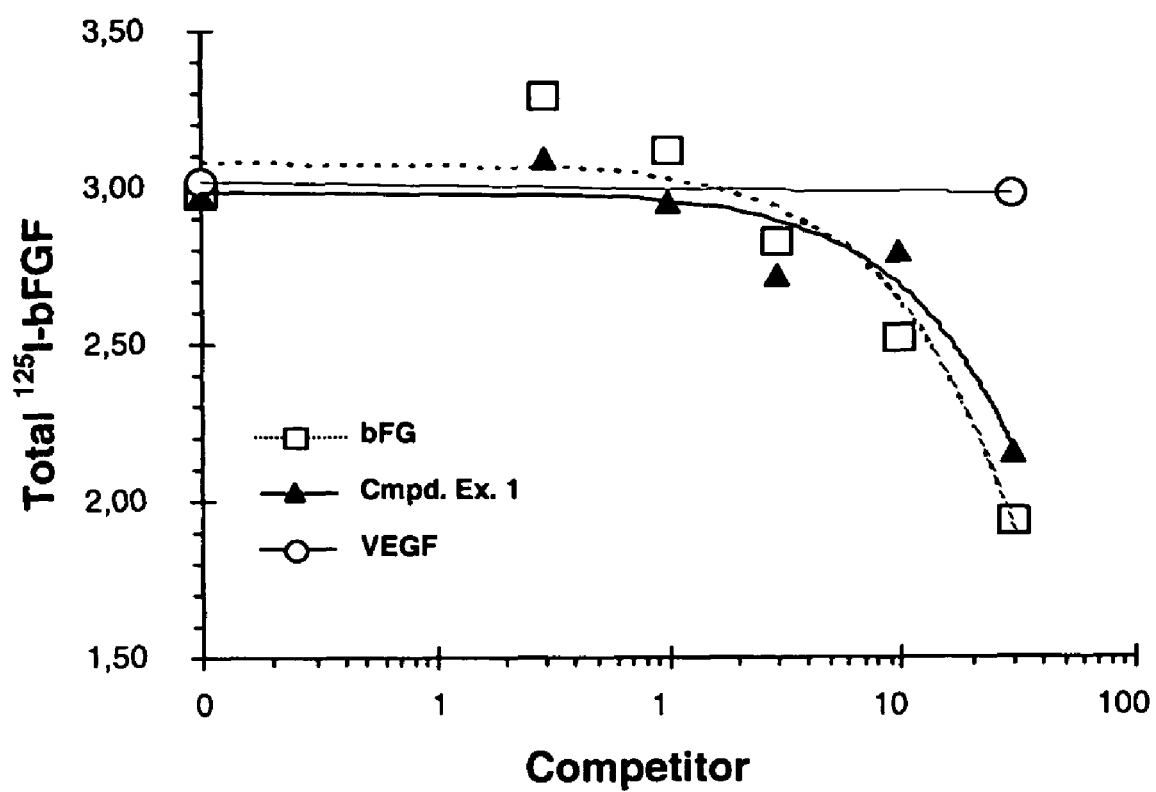
FIG. 3A is a graph depicting specific binding of the synthetic FGF analog of Example 1 (Cmpd. Ex 1) to FGFRs on HUVECs.

In particular embodiments of the present invention, the synthetic FGF analog of the present invention consists essentially of the molecule of formula I, i.e. the molecule of formula I is the major active component in the synthetic FGF analog composition.

The regions X and Z of the synthetic FGF analogs of formula I include amino acid residues, and optionally the region Y and, if provided, $R_2$, include amino acid residues. An amino acid residue is defined as —NHRCO—, where R can be hydrogen or any organic group. The amino acids can be D-amino acids or L-amino acids. Additionally, the amino acids can be α-amino acids, β-amino acids, γ-amino acids, or δ-amino acids and so on, depending on the length of the carbon chain of the amino acid.

The amino acids of the X, Y and Z component regions of the synthetic FGF analogs of the invention can include any of the twenty amino acids found naturally in proteins, i.e. alanine (Ala, A), arginine (Arg, R), asparagine (Asn, N), aspartic acid (Asp, D), cysteine (Cys, C), glutamic acid (Glu, E), glutamine (Gln, Q), glycine (Gly, G), histidine (His, H), isoleucine, (Ile, I), leucine (Leu, L), lysine (Lys, K), methionine (Met, M), phenylalanine (Phe, F), proline (Pro, P), serine (Ser, S), threonine (Thr, T), tryptophan (Trp, W), tyrosine (Tyr, Y), and valine (Val, V).

Furthermore, the amino acids of the X, Y and Z component regions of the synthetic FGF analogs of the invention can include any of the naturally occurring amino acids not found naturally in proteins, e.g. β-alanine, betaine (N,N,N-trimethylglycine), homoserine, homocysteine, γ-amino butyric acid, ornithine, and citrulline.

Additionally, the amino acids of the X, Y and Z component regions of the synthetic FGF analogs of the invention can include any of the non-biological amino acids, i.e. those not normally found in living systems, such as for instance, a straight chain amino carboxylic acid not found in nature. Examples of straight chain amino carboxylic acids not found in nature include 6-aminohexanoic acid, 7-aminoheptanoic acid, 9-aminononanoic acid and the like.

In formula I, two X regions are covalently linked to $R_1$, where $R_1$ is either a trifunctional amino acid residue, preferably a trifunctional alpha amino acid residue, or is a dipeptide of the formula $AA_1$-$AA_2$. Here and elsewhere, including in the claims, a group such as $R_1$ is "covalently bonded" to a group such as X when it is attached, directly or through intermediate atoms, the intermediate atoms optionally constituting another group, by way of covalent bonds. Thus X is covalently bonded or linked (the terms "covalently bonded" and "covalently linked" are synonymous) to $R_1$ when it is directed bonded by means of a single covalent bond, and is also covalently bonded or linked to $R_1$ when it is bonded by means of a series of covalent bonds and associated atoms, such as where $R_2$ is not zero.

Where $R_1$ is a trifunctional amino acid residue, X is covalently bonded to one functional group, W is covalently bonded to a second functional group, and the trifunctional amino acid residue is covalently bonded to $R_2$ by the third functional group. It is to be appreciated that such bonds may be to any chemically permitted functional group. For example, with a diamine amino acid, it is possible that one X is covalently bonded through the N-terminus amine group, the second X is covalently bonded through the epsilon amine of the side chain, and the diamine amino acid is covalently bonded to Y through the C-terminus carboxyl group. However, where the trifunctional amino acid residue is an amino acid with a reactive sulfhydryl side chain, such as cysteine, it is possible and contemplated that one X is covalently bonded through the N-terminus amine group, the second X is covalently bonded through the C-terminus carboxyl group, and the cysteine is covalently bonded to Y through the reactive sulfhydryl side chain. Similar approaches may be employed with other trifunctional amino acid residues, using cross-linkers as hereafter described.

Where $R_1$ is a dipeptide of the formula $AA_1$-$AA_2$, $AA_1$ can be any amino acid residue, including but not limited to a trifunctional amino acid residue, and $AA_2$ is a trifunctional amino acid residue. Thus one X region is covalently linked to $AA_1$, either through the N-terminus amine or alternatively, if $AA_1$ is a trifunctional amino acid residue, through the side chain, and the remaining X region is covalently linked through the side chain of $AA_2$. $AA_2$ is, in one preferred embodiment, a diamine amino acid.

The amino acid $AA_1$ of formula I can be any of amino acid, natural or unnatural. $AA_2$ can be any trifunctional amino acid residue, preferably a trifunctional alpha amino acid residue. In one a preferred embodiment, the trifunctional amino acid residue is a diamine amino acid, such as for instance lysine or ornithine, or any other amino acid having two amino groups.

The X regions of formula I of the synthetic FGF analogs of the present invention are a synthetic peptide chain that binds a FGFR. Region X can, for example, have any amino acid sequence that binds a FGFR, and can include amino acid sequences that are identical to a portion of the amino acid sequence of a FGF. Alternatively, X can have an amino acid sequence homologous rather than identical to a portion of the amino acid sequence of an FGF. The particular FGFR bound by the synthetic FGF analog of the invention may or may not be the cognate receptor of the original FGF, i.e. the synthetic FGF analog may additionally or solely bind to the receptor of a different FGF.

The term "homologous", as used herein refers to peptides that differ in amino acid sequence at one or more amino acid positions when the sequences are aligned. For example, the amino acid sequences of two homologous peptides can differ only by one amino acid residue within the aligned amino acid sequences of five to ten amino acids. Alternatively, two homologous peptides of ten to fifteen amino acids can differ by no more than two amino acid residues when aligned. In another alternative, two homologous peptides of fifteen to twenty or more amino acids can differ by up to three amino acid residues when aligned. For longer peptides, homologous peptides can differ by up to approximately 5%, 10%, 20% or 25% of the amino acid residues when the amino acid sequences of the two peptide homologs are aligned.

Particularly useful amino acid sequences as the X region of formula I includes homologs of fragments of naturally occurring FGFs that differ from the amino acid sequences of natural growth factor in only one or two or a very few positions. Such sequences preferably include conservative changes, where the original amino acid is replaced with an amino acid of a similar character according to well known principles; for example, the replacement of a non-polar amino acid such as alanine with valine, leucine, isoleucine or proline; or the substitution of one acidic or basic amino acid with another amino acid of the same acidic or basic character.

In another alternative, the X region of the synthetic FGF analog can include an amino acid sequence that shows no detectable homology to the amino acid sequence of any FGF. Peptides or growth factor analogs useful as components of the X region of the synthetic analogs of the present invention, that have little or no amino acid sequence homology with the cognate growth factor and yet bind FGFRs may be obtained by any of a wide range of methods, including for instance, selection by phage display. See as an example: Sidhu et al. Phage display for selection of novel binding peptides. Methods Enzymol. 328:333-63 (2000).

The X region of the synthetic FGF analogs of the invention can have any length that includes an amino acid sequence that effectively binds an FGFR. Preferably, the X region of the synthetic FGF analogs has a minimum length of at least approximately three amino acid residues. More preferably, the X region of the synthetic FGF analogs has a minimum length of at least approximately six amino acid residues. Most preferably the X region of the synthetic FGF analogs has a minimum length of at least approximately ten amino acid residues. The X region of the synthetic FGF analogs of the invention preferably also has a maximum length of up to approximately fifty amino acid residues, more preferably a maximum length of up to approximately forty amino acid residues, and most preferably a maximum length of up to approximately thirty amino acid residues.

The $R_2$ regions of formula I can include a chain of atoms or a combination of atoms that form a chain. Typically, the chains are chains primarily of carbon atoms, that may also optionally include oxygen or nitrogen atoms, such as for example chains of atoms formed from amino acids (e.g. amino acids found in proteins, as listed above; naturally occurring amino acids not found in proteins, such as ornithine and citrulline; or non natural amino acids, such as amino hexanoic acid; or a combination of any of the foregoing amino acids). It is also contemplated that agents such as polyethylene glycol (PEG), polyethylene oxide (PEO), amino polyethylene glycol, bis-amine-PEG, and other variants of polyethylene glycol known to those skilled in the art can similarly be used. Particularly preferred for the $R_2$ region are chains which include an amino terminal and a carboxyl terminal, such that the chains may be utilized in standard peptide synthesis methodologies. Examples include any amino acids, amino carboxylic acids, preferably straight chain amino carboxylic acids, and bifunctional amino-PEG-acid spacers. Among amino acids, glycine is preferred.

The chain of atoms of the $R_2$ region of formula I, if provided, is covalently attached to $R_1$ and X. The covalent bonds can be, for example, peptide, amide, thioether or ester bonds. If provided, the $R_2$ region preferably includes a chain of a minimum of about three atoms. For example, where the covalent bonds are peptide bonds, the $R_2$ region may be formed from a chain of at least one, at least two or at least three amino acids. However, where other than peptide bonds are employed, the $R_2$ region may further include a cross-linking moiety. For example, in formula II the $R_2$ region is a linker consisting of a sulfhydryl reactive homo-bifunctional cross linker and a second Cys, or alternatively includes a hetero-bifunctional cross-linker.

In one embodiment, the two X regions form a single linear peptide construct, separated by an $R_1$ group that is a trifunctional amino acid residue, optionally separated by both $R_2$ groups and an $R_1$ group. The trifunctional amino acid residue may, for example, have a reactive sulfhydryl group in the side chain, such as an L- or D-3-mercapto amino acid, including but not limited to L- or D-cysteine, L- or D-penicillamine, 3-mercapto phenylalanine, or a derivative of any of the foregoing. The $R_1$ trifunctional amino acid residue may be covalently bonded to the X regions by peptide bonds, such that the single linear peptide construct is, for example, X—C—X or X—$R_2$—C—$R_2$—X, where C is L- or D-cysteine, and each X or $R_2$, as the case may be, is covalently linked to C by peptide bonds. In one generalized description, this thus includes the following general formula:

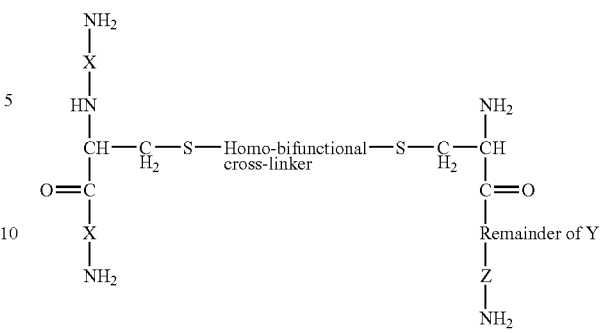

In this formula, the "homo-bifunctional cross-linker" forms a part of Y, together with the C residue to which the remainder of Y (if any) is covalently bonded. Any sulfhydryl reactive homo-bifunctional crosslinking agent may be employed, such as for example a maleimide cross-linker, a haloacetyl cross-linker or a pyridyl disulfide cross-linker.

A large number of such sulfhydryl cross-linkers, such as maleimide cross-linkers, are known. For example, in maleimide cross-linkers of the general formula:

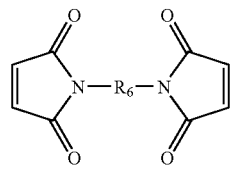

$R_6$ may be a $C_1$ to $C_8$ alkyl chain, such as for example 1,2-bis-maleimidoethane, 1,4-bis-malimidobutane or 1,6-bis-maleimidohexane, or may be an aryl group such as phenyl, such as for example 1,4-phenylene dimaleimide or 1,2-phenylene dimaleimide, or may be an aliphatic chain containing one or more oxygen (O), sulfur (S) or nitrogen (N) chain members, and optionally a ketone, such as for example dithio-bis-maleimidoethane, maleimidopropionic acid maleimidomethyl ester, bis-maleimidomethylether, 1,11-bis-maleimido-$(PEO)_4$, 1,8-bis-maleimido-$(PEO)_3$, and so on.

In yet another embodiment, any of a number of homo- or hetero-functional electrophilically-activated PEGs may be employed, including those that contain functional groups such as succinimidyl propionate, succinimidyl butanoate, N-hydroxysuccinimide, benzotriazol carbonate, aldehydes, acetaldehyde diethyl acetal, or vinylsulfone, and others known to those skilled in the art.

In yet another embodiment, a hetero-bifunctional cross-linker is employed. Hetero-bifunctional reagents which cross-link by two different coupling moieties can be particularly useful. Thus, the coupling moiety on $R_1$ is a cysteine residue and Y comprises a residue or other moiety with an amino group and a cross-linker for an amino group and sulfhydryl group, for example m-maleimidobenzoyl-N-hydroxysuccinimide ester. Alternatively the cross-linker reagent links two amino groups, for example N-5-azido-2-nitrobenzoyloxysuccinimide, an amino group and a carboxyl group, for example 4-[p-azidosalicylamido]butylamine, or an amino group and a guanadium group that is present in the side chain of arginine, for example p-azidophenyl glyoxal monohydrate.

In the synthetic FGF analogs of the present invention, in one preferred embodiment the Y region of formula I is a linker that is sufficiently hydrophobic to non-covalently bind the FGF analog to a polystyrene or polycaprolactone surface, or the like. In addition, the Y region may bind to other hydrophobic surfaces, particularly the hydrophobic surfaces formed from materials used in medical devices. Such surfaces are typically hydrophobic surfaces. Examples of suitable surfaces include but are not limited to those formed from hydrophobic polymers such as polycarbonate, polyester, polypropylene, polyethylene, polystyrene, polytetrafluoroethylene, expanded polytetrafluoroethylene, polyvinyl chloride, polyamide, polyacrylate, polyurethane, polyvinyl alcohol, polyurethane, poly ethyl vinyl acetate, poly(butyl methacrylate), poly(ethylene-co-vinyl acetate), polycaprolactone, polylactide, polyglycolide and copolymers of any two or more of the foregoing; siloxanes such as 2,4,6,8-tetramethylcyclotetrasiloxane; natural and artificial rubbers; glass; and metals including stainless steel, titanium, platinum, and nitinol. Preferably, the binding of the FGF analogs to the hydrophobic surface is of sufficient quantity to be detected by an analytical method such as an enzyme-linked immunoassay or a biological assay.

According to one embodiment of the invention, the Y region of formula I includes a chain of atoms or a combination of atoms that form a chain. Typically, the chains are chains of carbon atoms, that may also optionally include oxygen, nitrogen or sulfur atoms, such as for example chains of atoms formed from amino acids (e.g. amino acids found in proteins, as listed above; naturally occurring amino acids not found in proteins, such as ornithine and citrulline; or non-natural amino acids, such as an amino carboxylic acid; or a combination of any of the foregoing amino acids). Other mimetics of amino acids may similarly be employed, such as PEG, PEO, amino polyethylene glycol, bis-amine-PEG, and other variants of polyethylene glycol known to those skilled in the art. Particularly preferred for the Y region are chains which include an amino terminal and a carboxyl terminal, such that the chains may be utilized in standard peptide synthesis methodologies. Examples include any amino acids, amino carboxylic acids, preferably straight chain amino carboxylic acids, and bifunctional amino-PEG-acid spacers. Among amino acids, glycine is preferred.

The chain of atoms of the Y region of formula I is covalently attached to $R_1$ and to sequence Z. The covalent bonds can be, for example, peptide, amide, thioether or ester bonds. Particularly preferred is a peptide bond. Preferably, the Y region includes a chain of a minimum of about nine atoms. More preferably, the Y region includes a chain of a minimum of about twelve atoms. Most preferably, the Y region includes a chain of a minimum of about fifteen atoms. For example, the Y region may be formed from a chain of at least four, at least five or at least six amino acids. Alternatively, the Y region may be formed from a chain of at least one, at least two, or at least three amino carboxylic acids, such as aminohexanoic acid residues.

Preferably, the Y region includes a chain of a maximum of about fifty atoms. More preferably, the Y region includes a chain of a maximum of about forty-five atoms. Most preferably, the Y region includes a chain of a maximum of about thirty-five atoms. For example, the Y region may be formed from a chain of up to about twelve, up to about fifteen, or up to about seventeen amino acids.

The amino acid sequence of the Y region is preferably an artificial sequence, i.e. it does not include any amino acid sequence of four or more amino acid residues found in a natural ligand of a FGF.

In a particular embodiment, the Y region includes a hydrophobic amino acid residue, or a chain of hydrophobic amino acid residues. The Y region can, for example, include one or more amino carboxylic acid residues, such as one, two, three or more aminohexanoic acid residues. In another alternative embodiment, the Y region can include a combination of amino acid hydrophobic residues.

In another particular embodiment, the Y region of the molecule can include a branched or unbranched, saturated or unsaturated alkyl chain of between one and about twenty carbon atoms. In a further embodiment, the Y region can include a chain of hydrophilic residues, such as for instance, ethylene glycol residues. For instance, the Y region can include at least about three, or at least about four, or at least about five ethylene glycol residues.

The Z region of the molecule of formula I is a heparin-binding region and can include one or more heparin-binding motifs, BBxB or BBBxxB as described by Verrecchio et al. J.Biol.Chem. 275:7701 (2000). Alternatively, the Z region can include both BBxB and BBBxxB motifs (where B represents lysine, arginine, or histidine, and x represents a naturally occurring, or a non-naturally occurring amino acid). For example, the heparin-binding motifs may be represented by the sequence [KR][KR][KR]X(2)[KR] (SEQ ID NO:1), designating the first three amino acids as each independently selected from lysine or arginine, followed by any two amino acids and a sixth amino acid which is lysine or arginine.

The number of heparin binding motifs is variable. For instance, the Z region may include at least one, at least two, at least three or at least five heparin-binding motifs. Where there are more than one heparin-binding motifs, the motifs may be the same or different. Alternatively, the Z region includes up to a maximum of about ten heparin-binding motifs. In another alternative embodiment, the Z region includes at least four, at least six or at least eight amino acid residues. Further, in certain embodiments the Z region includes up to about twenty, up to about, twenty-five, or up to about thirty amino acid residues. It is to be realized that, in part, the avidity of the Z region for heparin is determined by the particular heparin-binding motifs selected and the number of such motifs in Z. Thus for particular applications both the selection and number of such motifs may be varied to provide optimal heparin binding of the Z region.

In a preferred embodiment, the amino acid sequence of the Z region is RKRKLERIAR (SEQ ID NO:2). In another embodiment, the amino acid sequence of the Z region is RKRKLGRIAR (SEQ ID NO:3). In yet another embodiment, the amino acid sequence of the Z region is RKRKLWRARA (SEQ ID NO:4). In yet another embodiment, the amino acid sequence of the Z region is RKRLDRIAR (SEQ ID NO:5). In yet another embodiment, the amino acid sequence of the Z region is RKRKLERIARC (SEQ ID NO:6). The presence of a terminal cysteine residue optionally affords the opportunity to link other molecules, including detection reagents such as fluorochromes, radioisotopes and other detectable markers, to the Z region, as well as the opportunity to link toxins, immunogens and the like.

Heparin-binding domains that bear little or no sequence homology to known heparin-binding domains are also contemplated in the present invention. As used herein the term "heparin-binding" means binding to the $—NHSO_3^-$ and sulfate modified polysaccharide, heparin, and also binding to the related modified polysaccharide, heparan. Such domains are contemplated to exhibit binding in physiological solutions including 0.15 M NaCl, and are expected to uncomplex at salt concentrations greater than 0.5 M NaCl.

The Z region of the synthetic FGF analogs of the present invention confers the property of binding to heparin in low salt concentrations, up to about 0.15 M NaCl, optionally up to about 0.48 M NaCl, forming a complex between heparin and the Z region of the factor analog. The complex can be dissociated in 1 M NaCl to release the synthetic FGF analog from the heparin complex.

The Z region is a non-signaling peptide. Accordingly, when used alone the Z region binds to heparin which can be bound to a receptor of FGF, but the binding of the Z region peptide alone does not initiate or block signaling by the receptor.

The C-terminus of the Z region may be blocked or free. For example, the C terminus of the Z region may be the free carboxyl group of the terminal amino acid, or alternatively, the C terminus of the Z region may be a blocked carboxyl group, such as for instance, an amide group.

As used here and elsewhere, the following terms have the meanings given.

The term "alkene" includes unsaturated hydrocarbons that contain one or more double carbon-carbon bonds. Examples of such alkene groups include ethylene, propene, and the like.

The term "alkenyl" includes a linear monovalent hydrocarbon radical of two to six carbon atoms or a branched monovalent hydrocarbon radical of three to six carbon atoms containing at least one double bond; examples thereof include ethenyl, 2-propenyl, and the like.

The "alkyl" groups specified herein include those alkyl radicals of the designated length in either a straight or branched configuration. Examples of such alkyl radicals include methyl, ethyl, propyl, isopropyl, butyl, sec-butyl, tertiary butyl, pentyl, isopentyl, hexyl, isohexyl, and the like.

The term "aryl" includes a monovalent or bicyclic aromatic hydrocarbon radical of 6 to 12 ring atoms, and optionally substituted independently with one or more substituents selected from alkyl, haloalkyl, cycloalkyl, alkoxy, alkythio, halo, nitro, acyl, cyano, amino, monosubstituted amino, disubstituted amino, hydroxy, carboxy, or alkoxy-carbonyl. Examples of an aryl group include phenyl, biphenyl, naphthyl, 1-naphthyl, and 2-naphthyl, derivatives thereof, and the like.

The term "aralkyl" includes a radical -$R^a R^b$ where $R^a$ is an alkylene (a bivalent alkyl) group and $R^b$ is an aryl group as defined above. Examples of aralkyl groups include benzyl, phenylethyl, 3-(3-chlorophenyl)-2-methylpentyl, and the like. The term "aliphatic" includes compounds with hydrocarbon chains, such as for example alkanes, alkenes, alkynes, and derivatives thereof.

The term "acyl" includes a group RCO—, where R is an organic group. An example is the acetyl group $CH_3CO$—.

A peptide or aliphatic moiety is "acylated" when an alkyl or substituted alkyl group as defined above is bonded through one or more carbonyl {—(C=O)—} groups. A peptide is most usually acylated at the N-terminus.

An "amide" includes compounds that have a trivalent nitrogen attached to a carbonyl group (—$CO.NH_2$).

An "amine" includes compounds that contain an amino group (—$NH_2$).

A "diamine amino acid" is an amino acid or residue containing two reactive amine groups and a reactive carboxyl group. Representative examples include 2,3 diamino propionyl amino acid residue, 2,4 diamino butylic amino acid residue, lysine or ornithine.

A "trifunctional amino acid" is an amino acid or residue with three reactive groups, one the N-terminus amine, a second the C-terminus carboxyl, and the third comprising all or a part of the side chain. Trifunctional amino acids thus include, by way of example only, diamine amino acids; amino acids with a reactive sulfhydryl group in the side chain, such as mercapto amino acids including cysteine, penicillamine, or 3-mercapto phenylalanine; amino acids with a reactive carboxyl group in the side chain, such as aspartic acid and glutamic acid; and amino acids with a reactive guanadium group in the side chain, such as arginine.

The synthetic FGF analogs represented by formula I, wherein X is an FGF analog, is a functional analog of an FGF, or portion thereof, which can be any FGF, such as any of the known FGFs, including all 23 FGFs from FGF-1 to FGF-23.

The fibroblast growth factors (FGFs) constitute a family of related proteins controlling normal growth and differentiation of mesenchymal, epithelial, and neuroectodermal cell types. Homologs have been found in a wide variety of species. FGFs show a very high affinity to heparin and are therefore also referred to as heparin-binding growth factors (HBGFs). As used herein, the term HBGFs includes all FGFs.

Two main types of FGF are known. The first type of FGF was isolated initially from brain tissue. It was identified by its proliferation-enhancing activities for murine fibroblasts, such as 3T3 cells. Due to its basic pI the factor was named basic FGF (bFGF, or HBGF-2, heparin-binding growth factor-2) and is now generally referred to as FGF-2. This is the prototype of the FGF family.

Another type of FGF, also initially isolated from brain tissues, is acidic FGF (aFGF, also known as HBGF-1, heparin-binding growth factor-1 or HBGF-α, heparin-binding growth factor-α), now generally referred to as FGF-1. It was identified by its proliferation-enhancing activity for myoblasts.

Other fibroblast growth factors belonging to the same family include FGF-3 (or HBGF-3, heparin-binding growth factor-3, originally called int-2; see Fekete, Trends in Neurosci. 23:332 (2000)), FGF-4 (HBGF-4, heparin-binding growth factor-4, initially recognized as the product of the oncogene hst; see Sakamoto et al., Proc. Natl. Acad. Sci. USA 91:12368-72), and FGF-5 (originally called HBGF-5, see Bates et al. Biosynthesis of human fibroblast growth factor 5. Mol. Cell. Biol. 11:1840-1845 (1991)); Burgess and Maciag, The heparin-binding (fibroblast) growth factor family of proteins. Ann. Rev. Biochem. 58: 575-606 (1989); and Zhan et al. The human FGF-5 oncogene encodes a novel protein related to fibroblast growth factors. Mol. Cell. Biol. 8:3487-3495 (1988)).

FGF-6 is also known as HBGF-6, and sometimes called hst-2 or oncogene hst-1 related growth factor; see Iida et al. Human hst-2 (FGF-6) oncogene: cDNA cloning and characterization. Oncogene 7:303-9 (1992); and Marics et al. Characterization of the HST-related FGF-6 gene, a new member of the fibroblast growth factor gene family. Oncogene 4:335-40 (1989).

FGF-7 or K-FGF is also known as KGF or keratinocyte growth factor (See Aaronson et al. Keratinocyte growth factor. A fibroblast growth factor family member with unusual target cell specificity. Annals NY Acad. Sci. 638:62-77 (1991)); Finch et al. Human KGF is FGF-related with properties of a paracrine effector of epithelial cell growth. Science 245:752-5 (1989); Marchese et al. Human keratinocyte growth factor activity on proliferation and differentiation of human keratinocytes: differentiation response distinguishes KGF from EGF family. J. Cellular Physiol. 144:326-32 (1990)).

FGF-8 was found to be identical to androgen-induced growth factor, AIGF and has been well studied (See Blunt et al. Overlapping expression and redundant activation of mesenchymal fibroblast growth factor (FGF) receptors by alternatively spliced FGF-8 ligands. J. Biol. Chem. 272:3733-8 (1997)); Dubrulle et al. FGF signaling controls somite boundary position and regulates segmentation clock control of spatiotemporal Hox gene activation. Cell 106:219-232 (2001); Gemel et al. Structure and sequence of human FGF8. Genomics 35:253-257 (1996); Tanaka et al. A novel isoform of human fibroblast growth factor 8 is induced by androgens and associated with progression of esophageal carcinoma. Dig. Dis. Sci. 46:1016-21 (2001)).

FGF-9 was originally called glia activating factor, or HBGF-9. See Miyamoto et al. Molecular cloning of a novel cytokine cDNA encoding the ninth member of the fibroblast growth factor family, which has a unique secretion pattern. Mol. Cell. Biol. 13:4251-9 (1993); and Naruo et al. Novel secretory heparin-binding factors from human glioma cells (glia-activating factors) involved in glial cell growth. J. Biol. Chem. 268: 2857-64 (1993).

FGF-10 is also called KGF-2, keratinocyte growth factor-2 (see Kok et al. Cloning and characterization of a cDNA encoding a novel fibroblast growth factor preferentially expressed in human heart. Biochem. Biophys. Res. Comm. 255:717-721, (1999)).

Several FGF-related factors have been described as fibroblast growth factor homologous factors (FHFs) and are also referred to as FGF-11 (FHF-3), FGF-12 (FHF-1), FGF-13 (FHF-2, see Greene et al. Identification and characterization of a novel member of the fibroblast growth factor family. Eur. J. Neurosci. 10:1911-1925 (1998)), and FGF-14 (FHF4).

FGF-15 is expressed in the developing nervous system and was identified as a gene regulated by transcription factor E2A-Pbx1. McWhirter et al. A novel fibroblast growth factor gene expressed in the developing nervous system is a downstream target of the chimeric homeodomain oncoprotein E2A-Pbx1. Development 124:3221-3232 (1997).

FGF-16 was isolated as a cDNA clone from rat heart by homology-based polymerase chain reaction expressing an FGF of 207 amino acids. FGF-16 is 73% identical to FGF-9. Miyake et al. Structure and expression of a novel member, FGF-16, of the fibroblast growth factor family. Biochem. Biophys. Res. Commun. 243:148-152 (1998).

The cDNA encoding FGF-17 was isolated from rat embryos and encodes a protein of 216 amino acids. When expressed in 3T3 fibroblasts, mouse FGF-17 is transforming. During embryogenesis, FGF-17 is expressed at specific sites in forebrain, the midbrain-hindbrain junction, the developing skeleton and in developing arteries. See Hoshikawa et al. Structure and expression of a novel fibroblast growth factor, FGF-17, preferentially expressed in the embryonic brain. Biochem. Biophys. Res. Commun. 244:187-191 (1998); and Xu et al. Genomic structure, mapping, activity and expression of fibroblast growth factor 17. Mechanisms of Development 83:165-178 (1999).

The cDNA encoding FGF-18 was isolated from rat embryos encoding a protein of 207 amino acids. FGF-18 is a glycosylated protein and is most similar to FGF-8 and FGF-17. Injection of recombinant murine FGF-18 has been shown to induce proliferation in tissues of both epithelial and mesenchymal origin, particularly in liver and small intestine. Recombinant rat FGF-18 induces neurite outgrowth in PC12 cells. Recombinant murine FGF-18 protein stimulates proliferation in NIH 3T3 fibroblasts in vitro in a heparan sulfate-dependent manner. For general information see Hu et al. FGF-18, a novel member of the fibroblast growth factor family, stimulates hepatic and intestinal proliferation. Mol. Cell. Biol. 18:6063-6074 (1998); and Ohbayashi et al. Structure and expression of the mRNA encoding a novel fibroblast growth factor, FGF-18. J. Biol. Chem. 273:18161-18164 (1998).

FGF-19 is related distantly to other members of the FGF family. FGF-19 mRNA is expressed in several tissues including fetal cartilage, skin, and retina, as well as adult gall bladder. It is overexpressed in a colon adenocarcinoma cell line. FGF-19 is a high affinity, heparin-dependent ligand for the FGF-4 receptor. See Xie et al. FGF-19, a novel fibroblast growth factor with unique specificity for FGFR4 Cytokine 11:729-735 (1999).

FGF-20 is expressed in normal brain, particularly the cerebellum, and in some cancer cell lines. FGF-20 mRNA is expressed preferentially in the substantia nigra pars compacta. Recombinant FGF-20 protein induces DNA synthesis in a variety of cell types and is recognized by multiple FGF receptors. FGF-20 functions like an oncogene, causing a transformed phenotype when expressed in the 3T3 fibroblast cell line. These transformed cells are tumorigenic in nude mice. See Jeffers et al. Identification of a novel human fibroblast growth factor and characterization of its role in oncogenesis. Cancer Res. 61:3131-8 (2001); and Ohmachi et al. FGF-20, a novel neurotrophic factor, preferentially expressed in the substantia nigra pars compacta of rat brain. Biochem. Biophys. Res. Commun. 277:355-60 (2000).

FGF-21 was isolated from mouse embryos. FGF-21 mRNA is most abundant in the liver with lower levels in the thymus. FGF-21 is most similar to human FGF-19. See Nishimura et al. Identification of a novel FGF, FGF-21, preferentially expressed in the liver. Biochim. Biophys. Acta 1492: 203-6 (2000).

The cDNA encoding FGF-22 (170 amino acids) was isolated from human placenta. FGF-22 is most similar to FGF-10 and FGF-7. Murine FGF-22 mRNA is expressed preferentially in the skin. FGF-22 mRNA in the skin is found preferentially in the inner root sheath of the hair follicle. See Nakatake et al. Identification of a novel fibroblast growth factor, FGF-22, preferentially expressed in the inner root sheath of the hair follicle. Biochim. Biophys. Acta 1517: 460-3 (2001).

FGF-23 is most similar to FGF-21 and FGF-19. The human FGF-23 gene maps to chromosome 12p13 linked to human FGF-6 gene. FGF-23 mRNA is expressed mainly in the brain (preferentially in the ventrolateral thalamic nucleus) and thymus at low levels. Missense mutations in the FGF-23 gene have been found in patients with autosomal dominant hypophosphataemic rickets. Overproduction of FGF23 causes tumor-induced osteomalacia, a paraneoplastic disease characterized by hypophosphatemia caused by renal phosphate wasting. See Yamashita et al. Identification of a novel fibroblast growth factor, FGF-23, preferentially expressed in the ventrolateral thalamic nucleus of the brain. Biochem. Biophys. Res. Commun. 277:494-8 (2000); and Shimada et al. Cloning and characterization of FGF23 as a causative factor of tumor-induced osteomalacia. Proc. Natl. Acad. Sci. (USA) 98:6500-5 (2001).

The X region of the molecule of formula I can include an amino acid sequence found in an FGF, such as for instance FGF-2 or FGF-7, or an amino acid sequence that is a homolog of a sequence found in an FGF. Alternatively, the X region can include a sequence not found in the natural ligand of the FGFR bound by the molecule.

The X region of synthetic FGF peptide analogs can include an amino acid sequence that is 100% identical to an amino acid sequence found in a fibroblast growth factor or an amino acid sequence homologous to an amino acid sequence of a fibroblast growth factor. For instance, the X region can include an amino acid sequence that is at least about 50%, at least about 75%, or at least about 90% homologous to an amino acid sequence from a fibroblast growth factor. The fibroblast growth factor can be any fibroblast growth factor, including any of the known or yet to be identified fibroblast growth factors.

In a particular embodiment, the synthetic FGF analog of the invention is an agonist of the FGFR. When bound to the FGFR, the synthetic FGF analog initiates a signal by the FGFR. In a further particular embodiment, the synthetic FGF analog of the invention is an antagonist of the FGFR. When bound to the FGFR, the synthetic FGF analog blocks signaling by the FGFR.

In another particular embodiment of the present invention, the synthetic FGF analog is an analog of FGF-2 (also known as basic FGF, or bFGF). In another particular embodiment of the present invention, the binding of the synthetic FGF analog to an FGF receptor initiates a signal by the FGF receptor. In a further particular embodiment, the binding of the synthetic FGF analog to the FGF receptor blocks signaling by the FGF receptor.

In a yet further particular embodiment, the present invention provides a synthetic FGF analog of FGF-2. In another particular embodiment, the present invention provides a synthetic FGF analog of FGF-2, wherein the amino acid sequence of the X region is YRSRKYSSWYVALKR (SEQ ID NO:7) from FGF-2. In yet another particular embodiment, the present invention provides a synthetic FGF analog wherein the amino acid sequence of the X region is NRFHSWDCIKTWASDTFVLVCYDDGSEA (SEQ ID NO:8). In yet another particular embodiment, the present invention provides a synthetic FGF-2 analog wherein the amino acid sequence of the X region is HIKLQLQAEERGVVS (SEQ ID NO:9).

In a yet further particular embodiment, the invention provides a synthetic FGF analog of FGF-1, wherein the X region is YISKKHAEKNWFVGLKK (SEQ ID NO:10). This sequence is derived from amino acids bridging the beta 9 and beta 10 loop of FGF-1. In yet another particular embodiment, an FGF-1 analog is provided wherein the X region is HIQLQLSAESVGEVY (SEQ ID NO:11), corresponding to amino acids derived from the β-4 and β-5 region of FGF-1.

In a yet further particular embodiment, the invention provides a synthetic FGF analog of FGF-7, wherein the X region is YASAKWTHNGGEMFVALNQK (SEQ ID NO:12). In yet another embodiment of a synthetic FGF analog of FGF-7, the X regions is the amino acid sequence YNIMEIRTVAVGIVA (SEQ ID NO:13).

Other FGF receptor binding domains, derived largely from targeting sequences in the C-terminus of human FGF, include the following sequences shown in Table 1:

TABLE 1

| CYTOKINE | PREFERRED X RECEPTOR BINDING DOMAIN |
|---|---|
| FGF-10 | YASFNWQHNGRQMYVALNQK (SEQ ID NO: 14) |
| FGF-22 | YASQRWRRRGQPNLALDRR (SEQ ID NO: 15) |
| FGF-9 | YSSNLYKHVDTGRRYYVALNK (SEQ ID NO: 16) |
| FGF-16 | YASTLYKHSDSERQYVALNK (SEQ ID NO: 17) |
| FGF-20 | YSSNIYKHGDTGRRFVALNK (SEQ ID NO: 18) |
| FGF-4 | YESYKYPGMFIALSKN (SEQ ID NO: 19) |
| FGF-6 | YESDLYQGTYILSKYGR (SEQ ID NO: 20) |
| FGF-12 | YSSTLYRQQESGRAWFLGNK (SEQ ID NO: 21) |
| FGF-14 | YSSMLYRQQESGRAWFLGLNK (SEQ ID NO: 22) |

TABLE 1-continued

| CYTOKINE | PREFERRED X RECEPTOR BINDING DOMAIN |
|---|---|
| FGF-13 | YSSMIYRQQQSGRGWYLGLNK (SEQ ID NO: 23) |
| FGF-11 | YASALYRQRRSGRAWYLDK (SEQ ID NO: 24) |
| FGF-1 | SNGGHFLRIL (SEQ ID NO: 28) |
| FGF-2 | KNGGFFLRIH (SEQ ID NO: 29) |
| FGF-7 | RTQWYLRID (SEQ ID NO: 30) |
| FGF-10 | FTKYFLKIE (SEQ ID NO: 31) |
| FGF-22 | STHFFLRVD (SEQ ID NO: 32) |
| FGF-9 | RTGFHLEIF (SEQ ID NO: 33) |
| FGF-16 | RTGFHLEIF (SEQ ID NO: 34) |
| FGF-20 | RTGFHLQIL (SEQ ID NO: 35) |
| FGF-4 | NVGIGFHLQAL (SEQ ID NO: 36) |
| FGF-6 | NVGIGFHLQVL (SEQ ID NO: 37) |
| FGF-12 | QQGYFLQMH (SEQ ID NO: 38) |
| FGF-14 | RQGYYLQMH (SEQ ID NO: 39) |
| FGF-13 | RQGYHLQLQ (SEQ ID NO: 40) |
| FGF-11 | RQGFYLQAN (SEQ ID NO: 41) |
| FGF-8 | RTSGKHVQVL (SEQ ID NO: 42) |
| FGF-17 | RTSGKHVQVT (SEQ ID NO: 43) |
| FGF-18 | RTSGKHIQVL (SEQ ID NO: 44) |
| FGF-3 | ATKYHLQLH (SEQ ID NO: 45) |
| FGF-5 | RVGIGFHLQIY (SEQ ID NO: 46) |
| FGF-19 | SGPHGLSSCFLRIR (SEQ ID NO: 47) |
| FGF-21 | DDAQQTEAHLEIR (SEQ ID NO: 48) |
| FGF-23 | ATARNSYHLQIH (SEQ ID NO: 49) |

Methods of Synthesizing the Heparin-Binding Growth Factor Analogs

The synthesis of the analogs of the invention can be achieved by any of a variety of chemical methods well known in the art. Such methods include bench scale solid phase synthesis and automated peptide synthesis in any one of the many commercially available peptide synthesizers. Preferably, the synthesizer has a per cycle coupling efficiency of greater than 99 percent.

The analogs of the present invention can be produced by stepwise synthesis or by synthesis of a series of fragments that can be coupled by similar well known techniques. See, for instance, Nyfeler, Peptide synthesis via fragment condensation. Methods Mol Biol 35:303-16 (1994); and Merrifield, Concept and early development of solid-phase peptide synthesis. Methods in Enzymol 289:3-13 (1997). These methods are routinely used for the preparation of individual peptides. It is thus possible to assemble the analogs of the present invention in component parts, such as peptides constituting the X—$R_3$—X or X—$R_2$—$R_1$—$R_2$—X and the Y-Z region components thereof, and to thereafter couple such component parts to assemble the analog. See, for instance, Dawson and Kent, Synthesis of native proteins by chemical ligation. Annu.

Rev. Biochem. 69:923-960 (2000); and Eom et al., Tandem ligation of multipartite peptides with cell-permeable activity. J. Am. Chem. Soc. 125:73-82 2003).

Advantageously, given that the analogs of formula I of the invention include two identical X region amino acid sequences, the synthesis of these identical X region peptides may be performed in parallel. By this method each cycle of addition adds an amino acid to both of the X region peptides, greatly facilitating the synthesis of these branched molecules. Synthesis in this manner is a particularly preferred method of making the analogs of formula I.

Peptide libraries that can be used to screen for a desired property, such as binding to an FGFR can be prepared by adaptations of these methods. See for instance, Fox, Multiple peptide synthesis, Mol. Biotechnol. 3:249-58 (1995); and Wade and Tregear, Solid phase peptide synthesis: recent advances and applications. Austral. Biotechnol. 3:332-6 (1993).

In a particular embodiment, the synthetic FGF analog of the invention is an agonist of the FGFR. When bound to the FGFR, the synthetic FGF analog initiates a signal by the FGFR. In another particular embodiment, the synthetic FGF analog of the invention is an antagonist of the FGFR. When bound to the FGFR, the synthetic FGF analog blocks signaling by the FGFR.

In a particular aspect, the invention provides a method for stimulating growth factor receptor signaling in a cell by contacting the cell with an effective amount of a synthetic FGF analog according to formula I. The effective amount can be readily determined by one of skill in the art. The signaling can result in cytokine release from the cell, stimulation or inhibition of proliferation or differentiation of the cell, chemotaxis of the cell, stimulation or inhibition of the immune system of the mammal.

Methods of Use of the FGFs of the Invention

The FGF analogs of the invention provide a cost effective and potentially unlimited source of biologically active molecules that are useful in a number of ways, including as soluble prophylactic or therapeutic pharmaceutical agents, such as for instance for administration as a soluble drug for prevention or treatment of various diseases, including for example, uses in cancer therapy and radioprotection.

The synthetic FGF analogs of present invention are also useful as biologically active agents for coating of medical devices, such as for instance, sutures, implants and medical instruments to promote biological responses, for instance, to stimulate growth and proliferation of cells, or healing of wounds.

Recombinant basic fibroblast growth factor (rFGF-2) has been widely studied with the goal of incorporating it into clinical regimens. While FGF-2 affects many cell types, its effect on angiogenesis underlies many of therapeutic approaches for it use. While rFGF-2 is currently approved only in Japan for the treatment of diabetic foot ulcers, it has continued to be explored for potential applications in a host of organs and diseases states. Examples of such applications include use in bone fracture healing and in bone void fillers, aneurysm healing and treatment, preparation of artificial organ implant sites and in the controversial area of therapeutic angiogenesis.

A synthetic peptide agonist of FGF-2 that stimulates angiogenesis, as well as endothelial cell proliferation and migration, has particular application in medical arenas where an insufficient or interrupted angiogenic response contributes to pathophysiology.

Bone, for example, is such an arena. During bone repair and insufficient or interrupted angiogenic response following injury inhibits osSEQus regeneration and is also thought to contribute to the pathophysiology of fibrous union, osteomyelitis, and osteoradionecrosis. The importance of angiogenesis in bone repair is reinforced by the ability of anti-angiogenic compounds to inhibit ectopic bone formation and by the ability of rFGF-2 to accelerate bone healing.

The term "medical device" as used herein means a device that has one or more surfaces in contact with an organ, tissue, blood or other bodily fluid in an organism, preferably a mammal, particularly, a human. Medical devices include, for example, extracorporeal devices for use in surgery such as blood oxygenators, blood pumps, blood sensors, tubing used to carry blood, and the like which contact blood that is returned to the patient. The term can also include endoprostheses implanted in blood contact in a human or animal body, such as vascular grafts, stents, pacemaker leads, heart valves, and the like that are implanted in blood vessels or in the heart. The term can further include devices for temporary intravascular use such as catheters, guide wires, and the like that are placed in blood vessels or the heart for purposes of monitoring or repair. The term can further include nerve electrodes, muscle electrodes, implantable pulse generators, implantable drug pumps, and defibrillators. Moreover, the term medical device can include sutures, graft materials, wound coverings, nerve guides, bone wax, aneurysm coils, embolization particles, microbeads, dental implants, bone prostheses, tissue scaffolds, artificial joints or controlled release drug delivery devices.

The surface of the medical device can be formed from any of the commonly used materials suitable for use in medical devices, such as for instance, stainless steel, titanium, platinum, tungsten, ceramics, polyurethane, polytetrafluoroethylene, extended polytetrafluoroethylene, polycarbonate, polyester, polypropylene, polyethylene, polystyrene, polyvinyl chloride, polyamide, polyacrylate, polyurethane, polyvinyl alcohol, polycaprolactone, polylactide, polyglycolide, polysiloxanes (such as 2,4,6,8-tetramethylcyclotetrasiloxane), natural rubbers, or artificial rubbers, or block polymers or copolymers thereof.

Methods for coating biological molecules onto the surfaces of medical devices are known. See for instance U.S. Pat. No. 5,866,113 to Hendriks et al., the specification of which is hereby incorporated by reference. Tsang et al. in U.S. Pat. No. 5,955,588 teach a non-thrombogenic coating composition and methods for using the same on medical devices, and is incorporated herein by reference. Zamora et al. in U.S. Pat. No. 6,342,591 teach an amphipathic coating for medical devices for modulating cellular adhesion composition, and is incorporated herein by reference.

In one embodiment the invention provides a method for delivering a synthetic FGF analog of formula I to a mammal, the method includes (i) providing a medical device coated on its surface with a synthetic FGF analog of formula I, the synthetic FGF analog being bound to the surface of the medical device by non-covalent bonds; and (ii) placing the medical device onto a surface of, or implanting the medical device into, the mammal.

In a particular embodiment of the above method, the non-covalent bonds are associations between the heparin binding domain of the synthetic FGF analog and a heparin-containing compound bound to the surface of the medical device. The heparin-containing compound bound to the surface of the medical device can be any heparin-containing compound, such as for instance, benzyl-bis(dimethylsilylmethyl)oxy carbamoyl-heparin (silyl heparin).

In another particular embodiment of the above method, the medical device is not pre-coated with a heparin-containing compound before being coated with the synthetic FGF analog of formula I.

In a particularly preferred embodiment, the medical device is an aneurysm coil or other vaso-occlusive device, and the synthetic FGF analog of the invention serves to induce endothelial cell attachment, proliferation and/or migration, and optionally further angiogenesis, such that a permanent and substantial blockage of the blood vessel into which the aneurysm coil or other vaso-occlusive device is placed results. Particularly preferred aneurysm coils include the Micrus MicroCoil System and Micrus ACT™ MicroCoil System (Micrus Corp., Sunnyvale, Calif.), and the aneurysm coils and vaso-occlusive devices described in U.S. Pat. Nos. 6,866,155, 6,835,185, 6,656,218, 6,656,201, 6,638,291, 6,616,617, 6,551,305, 6,416,541, 6,383,204, 6,306,153, 6,221,066, 6,171,326, 6,168,615, 6,165,194, 6,159,165, 6,136,015 and 6,102,932, incorporated here by reference as if set forth in full.

In yet another particularly preferred embodiment, the medical device incorporates therein a carrier material comprising a synthetic FGF analog of this invention. In one preferred embodiment, the medical device is an aneurysm coil, and the carrier material is a hydrogel comprising a growth factor which is a synthetic FGF analog of this invention. In this context, the teaching of U.S. Patent No. 6,113,629, describing a hydrogel for therapeutic treatment of aneurysms, is incorporated by reference as if set forth in full.

In yet another particularly preferred embodiment, the medical device is coated with a synthetic FGF analog of this invention by the methods disclosed in U.S. Patent Application No. 60/583,566, Bioactive Peptide Coatings, filed Jun. 28, 2004 and naming Paul O. Zamora and Sarah Albright as inventors, which application is incorporated here by reference as if set forth in full. It is to be understood that while U.S. patent application No. 60/583,566 primarily discloses methods utilizing synthetic heparin-binding growth factor analogs having two peptide chains branched from a dipeptide branch moiety composed of two trifunctional amino acid residues, which peptide chain or chains bind a heparin-binding growth factor receptor and are covalently bound to a non-signaling peptide that includes a heparin-binding domain by a hydrophobic linker, the methods of the invention may be employed with any of the synthetic FGF analogs of the invention, including those of formula I, and specifically including those in which two peptide chains are branched from a single trifunctional amino acid residue. In brief, the method thus includes, in a preferred embodiment, the steps of: a) contacting the medical device with a solution including a synthetic FGF analog of this invention; b) contacting the synthetic FGF analog-coated medical device with a solution comprising heparin or an analog thereof; and, c) contacting the product of step b) with a solution including a second synthetic FGF analog of the present invention, optionally wherein the second FGF analog is the same as the FGF analog of step a).

It is also possible and contemplated to coat a medical device by only employing step a) above, or by only employing steps a) and b) above. The solution comprising heparin or an analog thereof may be, in one embodiment, heparin in a buffer, aqueous solution. In another embodiment, the solution comprising heparin is a solution containing benzyl-bis(dimethylsilylmethyl)oxycarbamoyl-heparin. "Heparin" as used herein includes heparin, low-molecular-weight variants thereof, or fragments thereof, or any of a number of compounds that bind growth factors in a manner similar to heparin. Such compounds include but are not limited to heparan sulfate, chondroitin sulfate, hyaluronic acid, dextran sulfate, carboxymethyl cellulose, or any of a number of synthetic heparin-mimicking polyanionic compounds. "Heparin" also includes but is not limited to molecules including a mixture of variably sulfated polysaccharide chains composed of repeating units of d-glucosamine and either-iduronic or d-glucuronic acids, salts of any of the foregoing and derivatives of any of the foregoing. For example, conventional salts of heparin include sodium heparin, calcium heparin, magnesium heparin, and potassium heparin. Heparin derivatives include, but are not limited to ammonium heparin, benzalkonium heparin, and the like. Heparin further includes silyl-heparin compositions as described in U.S. patent application Ser. No. 10/450,309, entitled "Bioactive Coating Compositions and Methods", to Paul O. Zamora, et al., filed on Jan. 28, 2003, the specification of which is hereby incorporated by reference.

In an alternative embodiment, a synthetic FGF analog of this invention is allowed to react with a solution including heparin or an analog thereof, and a medical device is subsequently contacted with such solution. In a preferred embodiment, the FGF analog is a synthetic FGF analog of this invention and the medical device is an aneurysm coil. In another preferred embodiment the FGF analog is applied with a coating solution without further treatment.

The following described methods may be so employed, it being understood that different reagents, buffers and the like may be employed with the same or substantially similar results. In one method, aneurysm coils are coated by immersing in 10 mM sodium bicarbonate containing 1 μg/mL of a synthetic FGF analog of this invention for 1 hr at 37° C. The coils are rinsed in water and coated with heparin by immersing in 0.25% heparin in water for 30 minutes at room temperature. The coils are then rinsed in water and air-dried. In another method, aneurysm coils are coated by immersing in 10 mM sodium bicarbonate containing 1 μg/mL of a synthetic FGF analog of this invention for 1 hr at 37° C. The coils are rinsed in water and coated with 0.25% heparin in water for 30 minutes at room temperature. The coils are rinsed in water and then immersed in phosphate buffer (pH 5.8) containing 1 μg/mL of a synthetic FGF analog of this invention for 1 hour at 37° C. The synthetic FGF analog of this invention in phosphate buffer is preferably the same as the synthetic FGF analog of this invention in the sodium bicarbonate solution, but in an alternative embodiment the second synthetic FGF analog is different. The coils are then rinsed in water and air-dried. In yet a third method, aneurysm coils are coated by immersing in a solution of 10 mM sodium bicarbonate containing 1 μg/mL of synthetic FGF analog of this invention for 1 hour at 37° C. Separately, synthetic FGF analog of this invention, preferably the same but optionally different, in a 10 mM phosphate buffer (pH 5.8) is mixed with silyl-heparin in a 4:1 to 2:1 molar ratio for 1 hour at 37° C. The coils are then immersed in this solution, rinsed in water and air-dried.

Heparin-Binding Growth Factor Analog Pharmaceutical Applications

The FGF analogs of this invention can be used for as an active ingredient in pharmaceutical compositions for both medical applications and animal husbandry or veterinary applications. Typically, the FGF analog or pharmaceutical composition is used in humans, but may also be used in other mammals. The term "patient" is intended to denote a mammalian individual, and is so used throughout the specification and in the claims. The primary applications of this invention involve human patients, but this invention may be applied to laboratory, farm, zoo, wildlife, pet, sport or other animals.

The FGF analogs of this invention may be in the form of any pharmaceutically acceptable salt. The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganese, potassium, sodium, zinc, and the like. Particularly preferred are the ammonium, calcium, lithium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N, N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the FGF analog of the present invention is basic, acid addition salts may be prepared from pharmaceutically acceptable non-toxic acids, including inorganic and organic acids. Such acids include acetic, benzenesulfonic, benzoic, camphorsulfonic, carboxylic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and the like. Acid addition salts of the FGF analogs of this invention are prepared in a suitable solvent for the FGF analog and an excess of an acid, such as hydrochloric, hydrobromic, sulfuric, phosphoric, acetic, trifluoroacetic, citric, tartaric, maleic, succinic or methanesulfonic acid. The acetate salt form is especially useful. Where the FGF analogs of this invention include an acidic moiety, suitable pharmaceutically acceptable salts may include alkali metal salts, such as sodium or potassium salts, or alkaline earth metal salts, such as calcium or magnesium salts.

An FGF analog of the present invention may be complexed to any number of complex carbohydrate molecules which may bind to the heparin-binding domain of the FGF analogs and which include heparin, heparan sulfate, silyl-heparin, hyaluronic acid, chondroitin, chondroitin sulfate, carboxymethyl cellulose, dextran sulfate, sucrose octasulfate and cytodextrins. Such complex carbohydrates may be used to increase the molecular mass of an FGF analog, provide protection from proteases, modulate clearance from the body, provide binding to cellular targets, or to increase local resident times.

The invention provides a pharmaceutical composition that includes a FGF analog of this invention and a pharmaceutically acceptable carrier. The carrier may be a liquid formulation, and in one embodiment a buffered, isotonic, aqueous solution. Pharmaceutically acceptable carriers also include excipients, such as diluents, carriers and the like, and additives, such as stabilizing agents, preservatives, solubilizing agents, buffers and the like, as hereafter described.

Thus the FGF analog compositions of this invention may be formulated or compounded into pharmaceutical compositions that include at least one FGF analog of this invention together with one or more pharmaceutically acceptable carriers, including excipients, such as diluents, carriers and the like, and additives, such as stabilizing agents, preservatives, solubilizing agents, buffers and the like, as may be desired. Formulation excipients may include polyvinylpyrrolidone, gelatin, hydroxy cellulose, acacia, polyethylene glycol, manniton, sodium chloride and sodium citrate. For injection or other liquid administration formulations, water containing at least one or more buffering constituents is preferred, and stabilizing agents, preservatives and solubilizing agents may also be employed. For solid administration formulations, any of a variety of thickening, filler, bulking and carrier additives may be employed, such as starches, sugars, fatty acids and the like. For topical administration formulations, any of a variety of creams, ointments, gels, lotions and the like may be employed. For most pharmaceutical formulations, non-active ingredients will constitute the greater part, by weight or volume, of the preparation. For pharmaceutical formulations, it is also contemplated that any of a variety of measured-release, slow-release or time-release formulations and additives may be employed, so that the dosage may be formulated so as to effect delivery of a FGF analog of this invention over a period of time.

In practical use, the FGF analogs of the invention can be combined as the active ingredient in an admixture with a pharmaceutical carrier according to conventional pharmaceutical compounding techniques. The carrier may take a wide variety of forms depending on the form of preparation desired for administration, for example, oral, parenteral (including intravenous), urethral, vaginal, nasal, buccal, sublingual, or the like. In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that it may be administered by syringe. The form must be stable under the conditions of manufacture and storage and must be preserved against the contaminating action of microorganisms such as bacteria and fungi. The carrier can be a solvent or dispersion medium containing, for example, water, ethanol, a polyol, for example glycerol, propylene glycol or liquid polyethylene glycol, suitable mixtures thereof, and vegetable oils.

If the FGF analog pharmaceutical composition is administered by injection, the injection may be intravenous, subcutaneous, intramuscular, intraperitoneal or other means known in the art. The FGF analogs of this invention may alternatively be formulated by any means known in the art, including but not limited to formulation as tablets, capsules, caplets, suspensions, powders, lyophilized preparations, suppositories, ocular drops, skin patches, oral soluble formulations, sprays, aerosols and the like, and may be mixed and formulated with buffers, binders, excipients, stabilizers, anti-oxidants and other agents known in the art. In general, any route of administration by which the FGF analogs of invention are introduced across an epidermal layer of cells may be employed. Administration means may thus include administration through mucous membranes, buccal administration, oral administration, dermal administration, inhalation administration, nasal administration, urethral administration, vaginal administration, and the like.

In general, the actual quantity of FGF analog of this invention administered to a patient will vary between fairly wide ranges depending upon the mode of administration, the formulation used, and the response desired. The dosage for treatment is administration, by any of the foregoing means or any other means known in the art, of an amount sufficient to bring about the desired therapeutic effect.

The FGF analogs of the present invention may used for any condition, impairment, disease or syndrome for which inducing angiogenesis provides a therapeutic or palliative effect. Angiogenesis includes inducing vascularized tissue growth and physiological blood vessel formation. One particular application is angiogenesis at sites of ischemia, such as in the heart or a limb, to improve local or regional blood flow. In general, FGF-2 analogs of the present invention may be employed to limit, repair or reverse damage to ischemic tissues, both internal and external. Thus the FGF analogs may be employed for use in treatment of various intractable ulcers, including deep wound ulcers. Examples include bed sores, such as pressure-induced decubitus ulcers, ulcerative extremities, gangrenous extremities, diabetic ulcers and the like. Internal ulcers include oral mucosa ulcers, gastrointestinal ulcers, such as gastric ulcers, duodenal ulcers, or ulcers associated with trauma or other injury. The FGF-2 analogs may also be used to restore aspects of epithelial integrity in diseases and syndromes including those characterized by inflammation of the gastrointestinal tract, including conditions such as inflammatory bowel disease, ulcerative colitis and Crohn's disease.

The FGF analogs may thus be employed generally for wound healing, including surgically-induced, disease-induced and trauma-induced wounds. FGF analogs of the present invention may be employed to assist in healing of muscles, skin, bone, cartilage and other tissues of the body. In surgical procedures, FGF analogs may be employed to limit, prevent or treat abdominal wall incisional hernias or to reduce fascial wound failure. For certain of the foregoing, it may readily be seen that sustained release FGF analogs provide a therapeutic and practical advantage, and are included within the invention.

Injuries of the bone, which may be traumatic injuries and also include injuries resulting from diseases and degenerative conditions, that may be treated by FGF analogs of the present invention include fractures, open fractures, compound fractures, non-union fractures, segmental bone filling, boney voids, ischemic osteonecrosis, including avascular necrosis, and the like. The FGF analogs may also be employed in various orthopedic procedures, including procedures in which any device or fixture is intended to be fixed to bone, or any condition for which osteoinduction is desired. Thus, the FGF analogs may be employed for spinal fixation procedures using cages, rods, and other implants. FGF Analogs may be employed for other forms of spinal fusion and treatment of vertebral fractures and degenerative discs. The FGF analogs may be employed for joint replacement procedures, including but not limited to application as a coating component on joint prostheses. The FGF analogs may be employed for distraction osteogenesis and similar procedures for lengthening or otherwise altering bone. FGF analogs may also be employed in dental applications.

Injuries of the dermis may be treated by FGF analogs of the present invention, such as chemical, radiation or heat induced burns.

In another aspect, the FGF analogs of the present invention may be employed in treatment of various cardiovascular conditions. In one aspect, therapeutic angiogenesis induced by FGF analogs of the present invention serve to salvage chronically ischemic myocardium. In another aspect, the FGF analogs serve to increase cardiac resistance to injury and to guard against secondary injury after an acute ischemic insult, such as at the time of reperfusion. Thus depending on the disease state and the clinical objectives, the FGF analogs of the present invention may be employed either acutely or chronically. In another aspect, the FGF analogs serve to treat or ameliorate arterial occlusion.

In another aspect, the FGF analogs of the present invention may be employed to improve pulmonary function in patients with emphysema and other chronic obstructive pulmonary diseases. For pulmonary applications, the FGF analogs may be delivered as an aerosol of microparticles, or may be administered by intratracheal means, such as using controlled-release microspheres.

In another aspect, the FGF analogs of the present invention may be used for treatment or improvement of neurological deficits including in the treatment of Huntington's disease, Parkinson's disease, or Alzheimer's disease, and the like or after occlusive cerebrovascular disease.

The FGF analogs of the present invention may used in combination with other agents, including specifically bone marrow stromal cell transplantation.

The FGF analogs of the present invention have particular application in patients with compromised or reduced immune systems, and patients with diseases, such as diabetes, in which chronic or ischemic ulcers, wounds and the like are more common or in accelerating tissue transplants in such patients.

The invention is further illustrated by the following non-limiting examples.

EXAMPLE 1

A synthetic FGF analog, the structure of which is shown in FIG. 1, was synthesized by standard solid phase peptide synthesis methods. The FGF analog of FIG. 1 has a structure according to formula II, in which the amino acid sequences of the X region, AESGDDYCVLVFTDSAWTKICDWSHFRN (SEQ ID NO:25), corresponds to the reverse sequence of the C19 peptide sequence identified by Ballinger et al. (Nature Biotechnology 17:1199 (1999)). Each of the two X region peptides of SEQ ID NO:25 are covalently linked by amide bonds each to a different lysine residue, the lysine residues corresponding to $AA_1$ and $AA_2$. The $AA_2$ Lys was bound by means of a covalent peptide bond to one terminus of a tripeptide formed from three aminohexanoic acid residues and corresponding to linker Y, providing a hydrophobic space of 18 alkyl carbon atoms. The opposite terminus of the aminohexanoic acid tripeptide was covalently bound by a peptide bond to heparin-binding peptide RKRKLERIAR (SEQ ID NO:2) corresponding to region Z. The peptide of Example 1 was assembled stepwise by solid-phase The peptide of Example 1 was assembled stepwise by solid-phase synthesis on a substituted benzhydrylamine resin, using Fmoc chemistry for temporary protection of amino groups in the repetitive cycles. Branching of the chain was accomplished by stepwise growth of identical chains from the side-chain amino groups of consecutive lysyl residues. The completed peptide was cleaved from the resin as C-terminal amides by acidolysis, which also removed the acid-labile side-chain protecting groups.

The crude peptide preparation was first purified by heparin affinity chromatography. The crude preparation was solubilized in 10 mM HEPES (pH 7.0), loaded onto a HiTrap® Heparin HP column (Amersham Pharmacia Biotech, Piscataway, N.J., USA), and washed with 10 column volumes of 10 mM HEPES (pH 7.0). The peptide was then eluted with 2 M NaCl in 10 mM HEPES (pH 7.0), monitored by 280 nm absorbance. Peptide fractions were desalted and concentrated by loading onto Sep-Pak® C$_{18}$ cartridges (Waters, Milford, Mass., USA), washed with 10 column volumes of water, and then eluted with 80% acetonitrile. Eluted fractions were lyophilized, redissolved in water, and the concentration was determined by BCA® Protein Assay Kit (Pierce Endogen, Rockford, Ill., USA) using bovine serum albumin as a reference.

EXAMPLE 2

The synthetic FGF analog as shown in FIG. 2, was synthesized by standard solid phase peptide synthesis methods. The amino acid sequences of Example 2 corresponding to regions Y and Z of formula I are identical to those of the compound of Example 1. The amino acid sequence RKLAVY-WSSYKRSRY (SEQ ID NO:26) of the two X region peptides correspond to the reverse sequence of amino acids 115-129 of FGF-2 identified by Ray et al. (Proc. Natl. Acad. Sci. USA 94:7047-7052, 1997). The crude preparation was purified as described above in Example 1.

EXAMPLE 3

The synthetic FGF analog H-K(H-YRSRKYSSWY-VALKR)-K(H-YRSRKYSSWYVALKR) -Ahx-Ahx-Ahx-RKRKLERIAR-NH$_2$ was synthesized by standard solid phase peptide synthesis methods as in Example 1 wherein YRSRKYSSWYVALKR is SEQ ID NO:7, and RKRKLERIAR is SEQ ID NO:2. It is to be understood that "Ahx" and "Hex" are used interchangeably, have the same meaning, and refer to aminohexanoic acid. In the formula H-K(H-YRSRKYSSWYVALKR)-K(H-YRSRKYSSWYVALKR)-Ahx-Ahx-Ahx-RKRKLERIAR-NH$_2$, each "H-" represents a hydrogen atom, such that the N-terminus of each X chain, and the N-terminus of the lysine at AA$_1$, is NH$_2$. The compound of Example 3 was identical to that of Example 2, except that the normal, or non-reverse, sequence YRSRKYSWYVALKR (SEQ ID NO:7) was employed, corresponding to the sequence of amino acids 115-129 of FGF-2 identified by Ray et al. (Proc. Natl. Acad. Sci. USA 94:7047-7052, 1997). The amino acid sequences of the compound of Example 3 corresponding to regions Y and Z of formula I are identical to those of the compound of Example 2. The crude preparation was purified as described above in Example 1. The peptide of Example 3 has an estimated molecular weight of 5809.

The general structure of the compound of Example 3 is shown below:

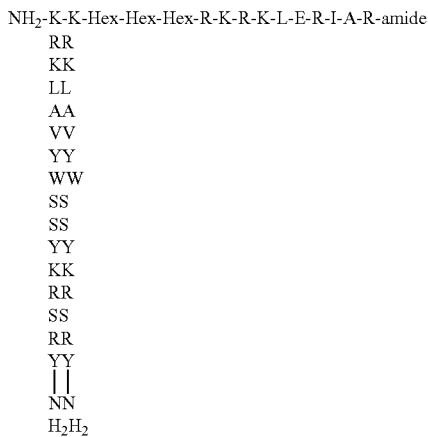

wherein YRSRKYSSWYVALKRK is SEQ ID NO:7 and wherein RKRKLERIAR is SEQ ID NO:2

EXAMPLE 4

The synthetic FGF analog YRSRKYSSWYVALKRK(H-YRSRKYSSWYVALKR)-Ahx-Ahx-Ahx-RKRLDRIAR-NH$_2$ was synthesized by standard solid phase peptide synthesis methods as in Example 1. In the compound YRSRKYSSWYVALKRK(H-YRSRKYSSWYVALKR)-Ahx-Ahx-Ahx-RKRILDRIAR-NH$_2$, the R$_1$ group of formula I was a single trifunctional amino acid residue, here a diamine amino acid, lysine (K). The compound of Example 4 was otherwise identical to that of Example 3, with the amino acid sequences of the compound of Example 4 corresponding to regions Y and Z of formula I identical to those of the compound of Example 2 or 3. The peptide of Example 4 has an estimated molecular weight of 5681.

The peptide of Example 4 was assembled stepwise by solid-phase synthesis on a substituted resin, using Fmoc chemistry for temporary protection of amino groups in the repetitive cycles. Protecting groups were used as required. Branching of the chain was accomplished by stepwise growth of identical chains from the alpha amino group and side-chain amino group of a single lysyl residue. The completed peptide chain was cleaved from the resin as C-terminal amides by acidolysis, which also removed the acid-labile side-chain protecting groups. The peptide of Example 4 was purified by reverse phase HPLC using a C$_{18}$ column in a continuous gradient elution of 0-60% B over 60 minutes, run at 1 mL/min, where A was 0.1% trifluoroacetate in water and B was 0.1% trifluoroacetate in acetonitrile. The general structure of the compound of Example 4 is shown below:

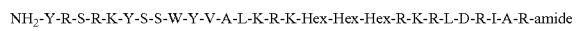
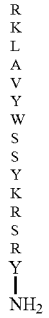

wherein YRSRKYSSWYVALKRK is SEQ ID NO:7 and RKRLDRIAR is SEQ ID
NO:5.

EXAMPLE 5

Figure 3B:
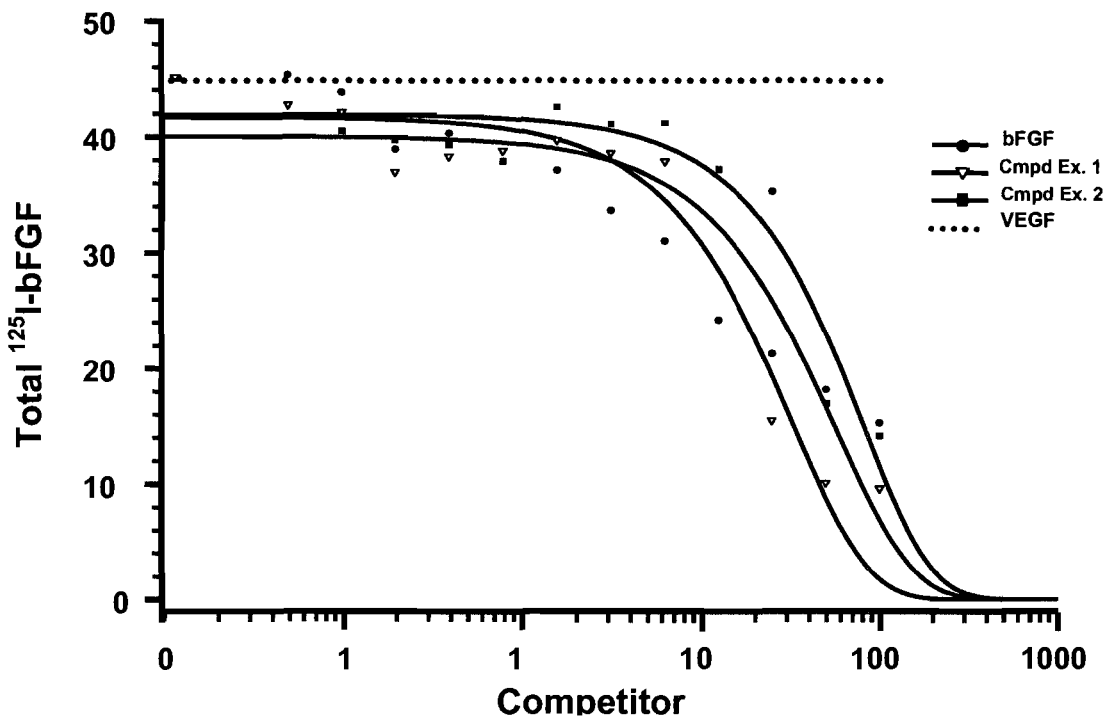
FIG. 3B is a graph depicting specific binding of the synthetic FGF analog of Examples 1 and 2 (Cmpd. Ex 1 and Cmpd. Ex. 2) to FGFRs on C3H10T1/2 fibroblasts according to one embodiment of the present invention.

FIG. 3A shows the specific binding of the Compound of Example 1 to HUVECs (human umbilical vein endothelial cells). [125]I-bFGF was incubated with intact HUVECs in the presence of unlabeled Compound of Example 1. The bound [125]I-bFGF fraction at 4° C. was recovered from solubilized HUVEC membranes after stringent washing and quantitated in a gamma counter. Compound of Example 1 displaced [125]I-bFGF (FGF-2) bound to FGF receptors of the HUVECs, while the unrelated heparin-binding cytokine, VEGF did not. FIG. 3B shows that Compound of Example 1 and Example 2 competitively displaced [125]I-bFGF binding to a second series of cells containing FGF receptors, while the unrelated heparin-binding cytokine VEGF did not. $^{125}$I-bFGF was incubated with cultured C3H10T1/2 fibroblasts in the presence of cold Compound of Example 1 and Example 2 for 20 minutes on ice. After stringent washing, the bound $^{125}$I-bFGF fraction at 4° C. was recovered from solubilized cell membranes and quantitated in a gamma counter.

EXAMPLE 6

Figure 4:
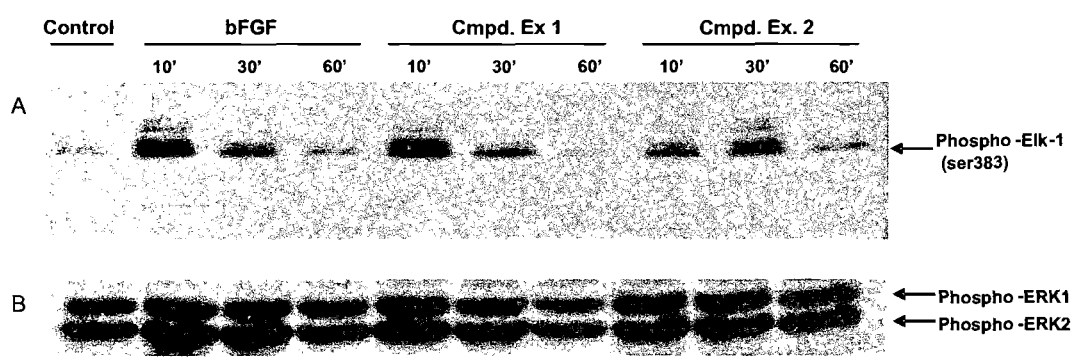
FIG. 4 is a blot illustrating the equivalence of the synthetic FGF analog of Examples 1 and 2 (Cmpd. Ex 1 and Cmpd. Ex 2) to native, recombinant FGF-2 in MAP kinase phosphorylation and activation according to one embodiment of the present invention.

FIG. 4 shows the equivalence of FGF-2 analog Compounds of Example 1 and Example 2 to native, recombinant FGF-2 in MAP kinase phosphorylation and activation. C3H10T1/2 cells were stimulated with 3 nM of FGF-2, Compound of Example 1 or Example 2 for 10, 30 or 60 minutes and lysed. Active MAP kinase from cell lysates were immunoprecipitated with monoclonal anti-phosphop-44/42 MAP kinase (Thr202 and Tyr204). The resulting immunoprecipitate was incubated with an Elk-1 fusion protein in the presence of ATP. Phosphorylated Elk-1 at Ser383 was visualized by western blotting using a phosphor-Elk-1 (Ser 383) antibody. To reveal the phosphorylation of MAP kinase, cell lysates were analyzed by western blotting using monoclonal anti-phosphop-44/42 MAP kinase (Thr202 and Tyr204) antibody. The results show that both Compound of Example 1 and Example 2 activate Elk-1, as does FGF-2, as shown by the phosphorylated Ser383 residue present in these samples at 10 minutes and absent from the untreated control. The level of phosphorylated Ser383 decreased successively from 10 minutes to 30 minutes and even further at 60 minutes. By contrast, the level of phosphor-ERK-1 and phosphor-ERK-2 was consistently high in the Compounds of Ex. 1 (F2A3), and the Compounds of Ex. 2 (F2A4) treated samples at 10 minutes, 30 minutes and 60 minutes, whereas the control untreated sample exhibited a distinguishably lower level of each of phosphor-ERK-1 and phosphor-ERK-2. These observations show that the FGF analogs and Compounds of Example 1 and Example 2 are biologically active as FGF-2 analogs in these assays.

EXAMPLE 7

Figure 5:
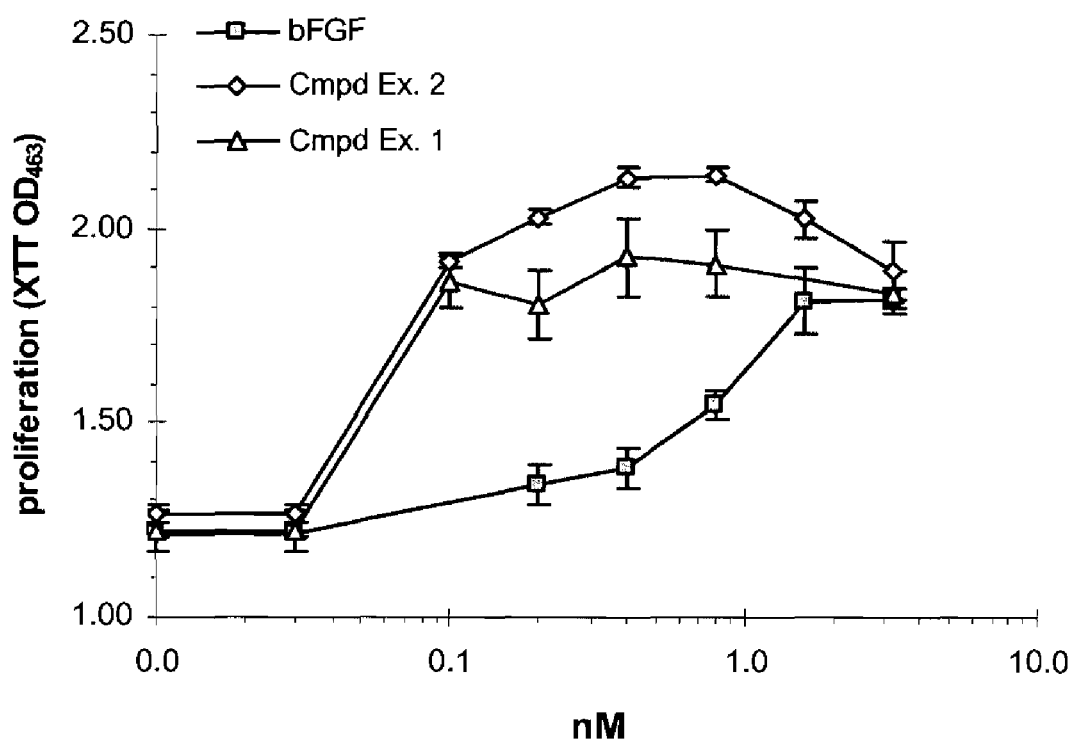
FIG. 5 is a graph according to one embodiment of the present invention of stimulation of cell proliferation in fibroblast cultures; illustrating the mitogenic dose response of the synthetic FGF analog of Examples 1 and 2 (Cmpd. Ex 1 and Cpmd. Ex 2) versus FGF-2.

FIG. 5 shows the results of an assay for mitogenesis by Compounds of Example 1 and Example 2 as compared with bFGF (FGF-2). C3H10T1/2 cells were grown in DMEM medium supplemented with 10% FBS (fetal bovine serum). Two days before the assay, cell culture medium was replaced with low serum medium (DMEM with 0.1% FBS). At the start of the assay, cells were trypsinized and a single-cell suspension was seeded onto 96-well culture plates at 1,000 cells/well. Compounds of Example 1 or 2 or recombinant human FGF-2 were added to triplicate wells (100 µL/well final volume), and culture plates were returned to a 37° C. incubator. After three days, cell proliferation was quantified by the XTT Cell Proliferation Kit II (Roche Applied Science, Indianapolis, IN, USA) according to manufacturer's instructions.

Compounds of Example 1 and Example 2 provided higher specific activities at lower concentrations than FGF-2 as shown by the results of this assay.

EXAMPLE 8

Figure 6A:
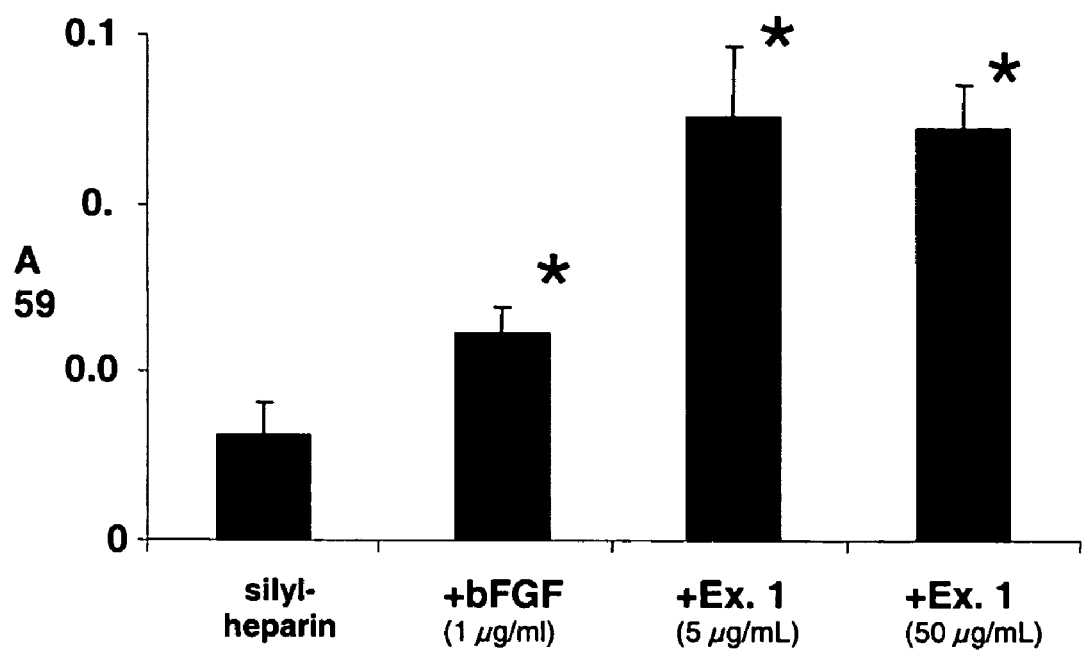
FIG. 6A is a plot according to one embodiment of the present invention illustrating that synthetic FGF analog of Examples 1 and 2 mimic FGF-2 for cell attachment in vitro, showing attachment, after two hours, of CH310T1/2 murine fibroblasts to polystyrene coated with silyl-heparin alone or with silyl-heparin plus the synthetic FGF analog of Examples 1 and 2. (*) indicates p less than 0.05.
Figure 6B:
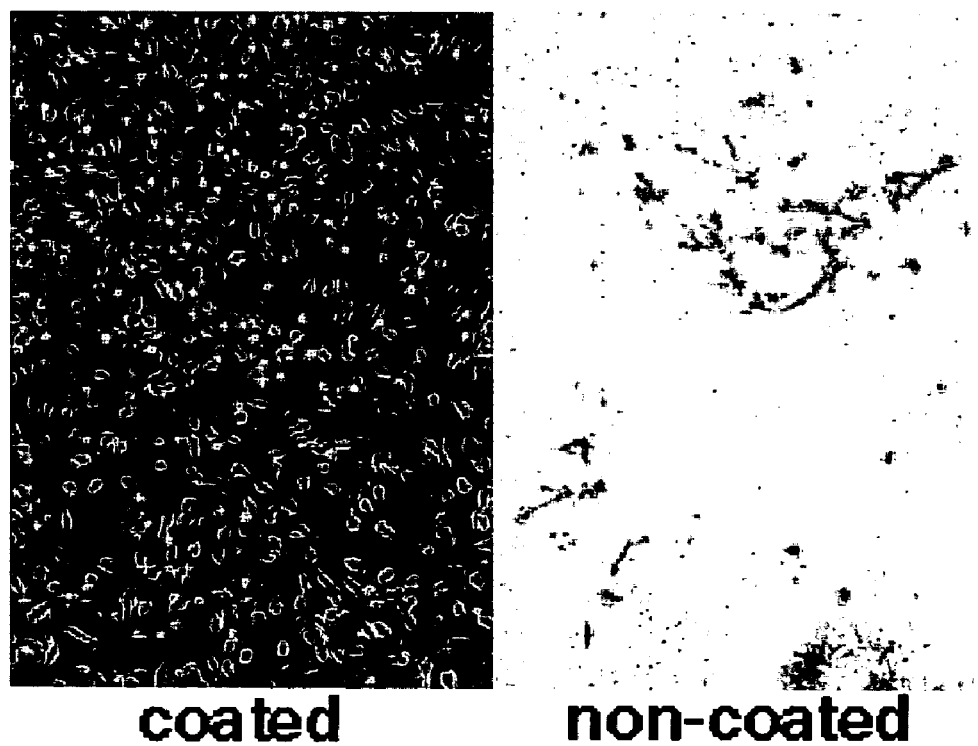
FIG. 6B is a micrograph of bovine aortic endothelial cells grown on polycaprolactone with (left panel) and without (right panel) a coating of the synthetic FGF analog of Example 1.

FIG. 6 shows enhancement of attachment in vitro by Compound of Example 1. Attachment of C3H10T1/2 murine fibroblasts to the wells of a polystyrene 96-well tissue culture plate coated with silyl-heparin alone or with silyl-heparin plus bFGF (FGF-2) or silyl-heparin plus Compound of Example 1 at the indicated concentrations was measured by absorbance at 595 nm after 2 hours.

Micrographs of bovine aortic endothelial cells (BEACs) grown on polycaprolactone with or without a coating of Compound of Example 1 were obtained. Cells were stained with crystal violet and photographed at 100× magnification. A substantially higher cell density of attached cells on the Compound of Example 1 coated specimen was observed.

EXAMPLE 9

Figure 7A:
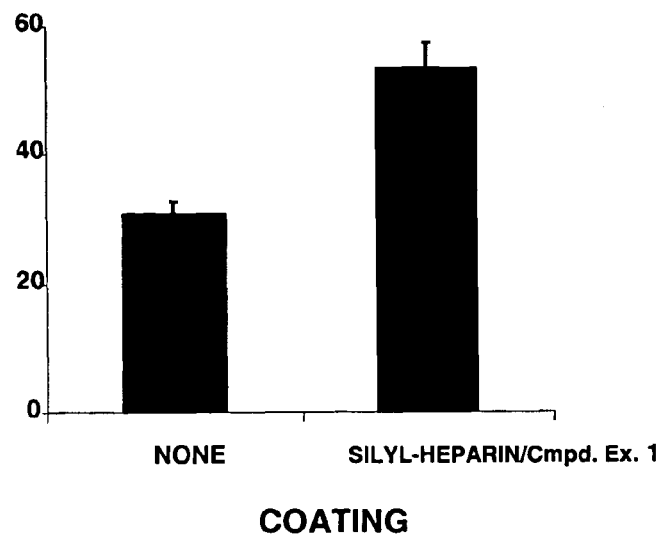
FIG. 7A is a plot according to one embodiment of the present invention illustrating the comparison of capillaries/field utilizing coated polylactide sutures in rat muscle at 2 weeks, comparing no coating, panel B as silyl heparin coating, panel C is a Compound for Example 1 coating, and panel D is a silyl heparin and Compound of Example 1 coating.
Figure 7B:
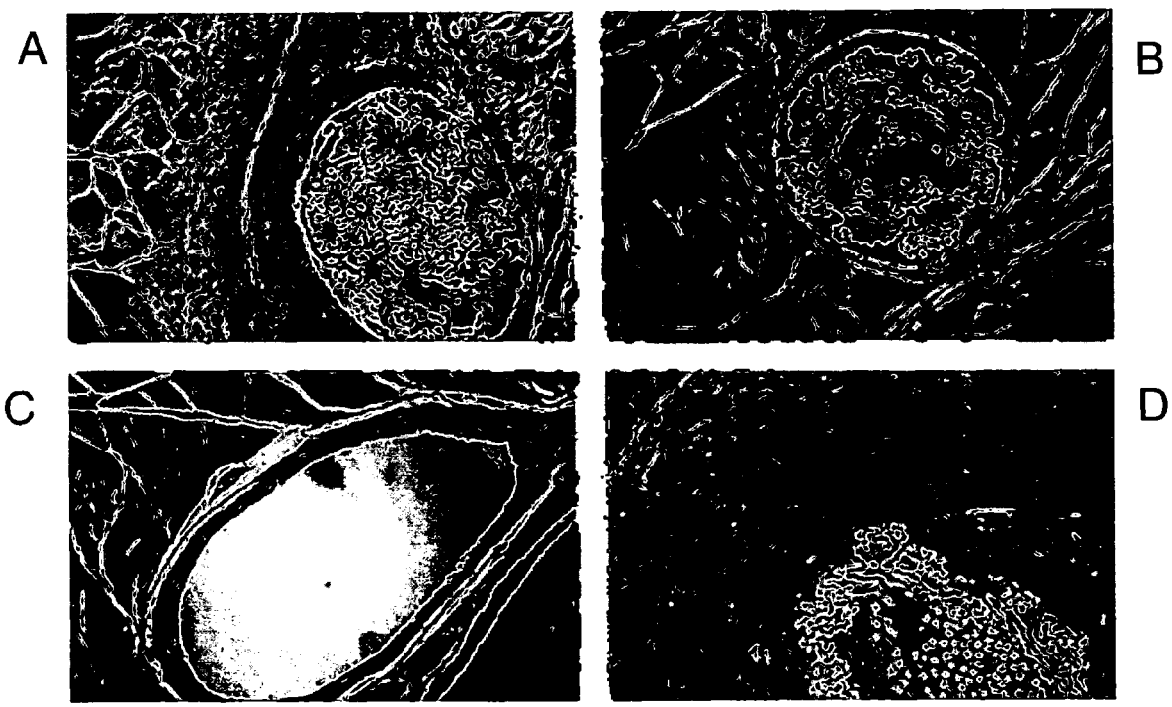

FIG. 7 shows the promotion of wound healing by locoregional delivery of Compound of Example 1 on biodegradable sutures. Bioabsorbable Vicryl® polyglycolide/lactide sutures (Ethicon Johnson & Johnson, Somerville, N.J., USA) coated to saturation with a combination silyl-heparin and Compound of Example 1 and without any coating were introduced into the thigh muscle of adult rats. After two weeks the implanted area was removed and processed for histology by routine methods. The capillaries were quantitated at a magnification of 100× and the data expressed as the average per field; as shown in FIG. 7, the Y axis depicts the number of capillaries per field. Increased granulation and angiogenesis were also observed utilizing H&E stained histological sections. Microscopic examination revealed a moderate amount of granulation after 2 weeks of rat muscle tissue where an uncoated suture was introduced. With both silyl-heparin coated sutures and Compound of Example 1 coated sutures, low to moderate granulation was found. With sutures coated with silyl-heparin and Compound of Example 1, braided PGLA fibers were evident in cross section, surrounded by a ring of granulation tissue of varying thickness, within a field of striated muscle tissue. Both silyl-heparin alone and Compound of Example 1 alone coatings reduced cellularity, compared to the control. But the combination of silyl-heparin and Compound of Example 1 caused marked fibroblast proliferation surrounding and infiltrating the braided suture, and increased endothelial cells within the granulation tissue.

EXAMPLE 10

Figure 8:
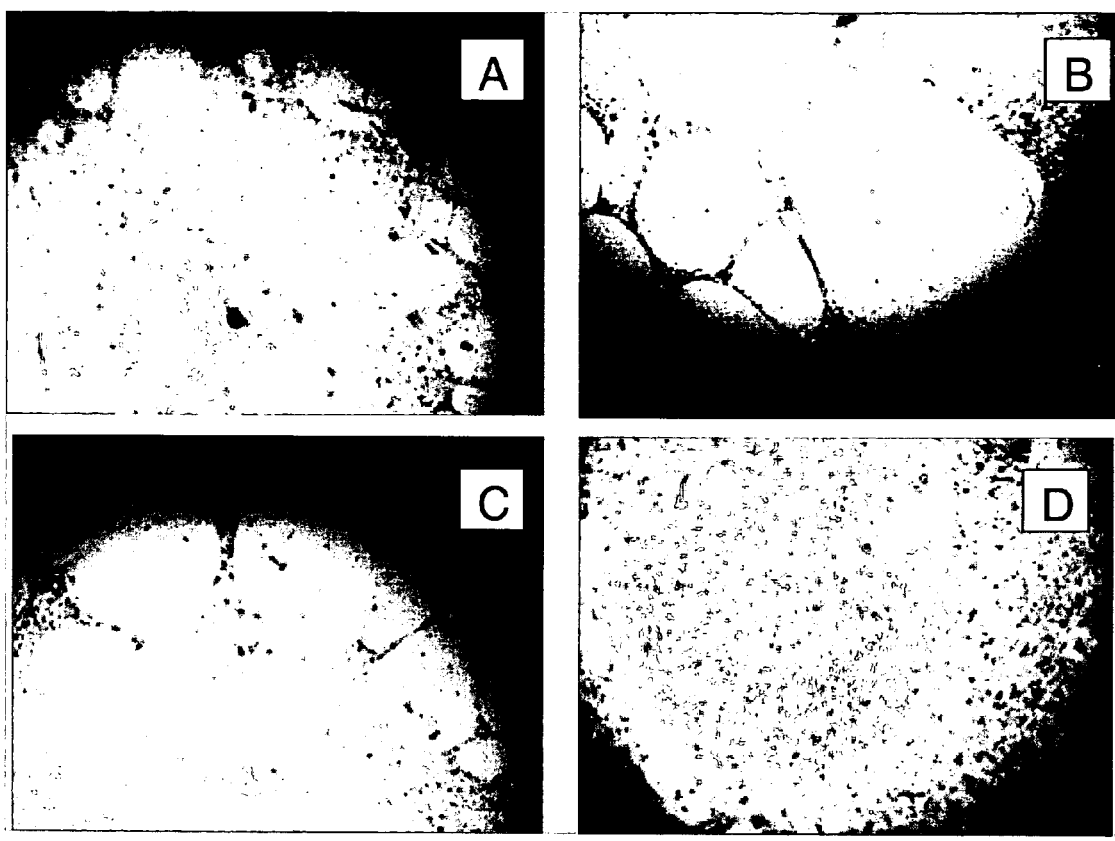
FIG. 8 are micrographs of tube formation by human umbilical vein endothelial cells (HUVECs) treated with Compound of Example 3 and 4 according to one embodiment of the present invention. HUVECs were grown on Matrigel and stimulated with 100 ng/mL of FGF-2 (A), 50 ng/mL Compound of Example 3 (B) or Compound of Example 4 (C), or left untreated as controls (D). After 24 hours the cultures were fixed and stained with Toluidine blue O; original magnification 40×.

Human umbilical vein endothelial cells (HUVECs) were seeded at 5×10$^5$ cells on a layer of previously polymerized Matrigel with or without peptides or FGF-2 (R&D Systems, Minneapolis, Minn.) that was used as a positive control. Matrigel (BD Biosciences division of Becton, Dickenson and Company) is a solubulized basement membrane preparation extracted from EHS mouse sarcoma. According to the vendor its major component is laminin, followed by collagen IV, heparan sulfate proteoglycans, and entactin. At room temperature, Matrigel polymerizes to produce matrix material resembling the basement membrane and has been used as a substrate for in vitro endothelial cell invasion and tube formation assays as well to assess in vivo angiogenic activity of different compounds. In these studies, the medium was composed of DMEM:F12 containing 2% serum. Matrigel cultureware incubated at 37° C. After 24 hours, changes of cell morphology were captured through a phase-contrast microscope and photographed. As shown in FIG. 8, use of Compounds of Example 3 or 4 with HUVECs resulted in an increase in tube formation. FGF-2, used as a system control, caused tube formation at 100 ng/mL, but had only a marginal effect at 50 ng/mL.

EXAMPLE 11

HUVECs and C3H10T1/2 cells were used as target cells and two different methods were used in the analysis, migration across a wound margin and migration through a coated membrane (21). For studies involving migration across a wound margin, the cells were grown in vitro and used when approximately 90% confluent. A simulated wound was made by scrapping the cells away from the substrate. The cultures were rinsed and then incubated in DMEM: F12 medium containing 2% newborn calf serum with or without peptide. FGF-2 (50 ng/mL) was used as a positive control reference material. The cells were allowed to migrate for 6 hours after which the cells were fixed in buffered formalin. Migration was monitored via phase contrast microscopy. Migrating cells were those that had migrated across the site of the simulated wound margin. For studies involving migration through a coated membrane, the bottoms of trans-well inserts (3 micron pore size) were coated with a solution of Matrigel and allowed to dry. Target cells were then placed in the upper chamber and the inserts placed into wells containing medium with or without peptide. The cultures were maintained for 18 hours after which the cells in the upper chamber were removed and the specimens fixed in buffered formalin. The cells on the lower side of the insert were then stained with bis-benzamide and the cells quantitated using fluorescence microscopy. Compound of Example 4 was evaluated for its ability to cause cellular migration using both HUVECs and C3H10T1/2 cells. Compound of Example 4 caused an increase in vitro migration of HUVECs across a simulated wound margin at 50 and 100 ng/mL, as shown in Table 2. FGF-2, which was used as a positive control compound, also induced migration.

TABLE 2

| peptide | ng/mL | cells/field | s.d. | p = |
|---|---|---|---|---|
| none | 0 | 33.7 | 9.7 | |
| FGF-2 | 50 | 50.3 | 5.2 | 0.023 |
| Compound Example 4 | 1 | 36.0 | 8.2 | 0.990 |
| Compound Example 4 | 5 | 39.7 | 4.5 | 0.880 |
| Compound Example 4 | 50 | 58.6 | 12.5 | <0.001 |
| Compound Example 4 | 100 | 48.1 | 9.0 | 0.041 |

Statistical significance was determined using ANOVA followed by post hoc testing (Tukey). An increase in migration C3H10T1/2 cells across a simulated wound margin was also found at similar concentrations (data not presented). Transwell migration was also increased in HUVECs and C3H10T1/2, as shown in Table 3:

TABLE 3

| | | migrated cells as % of control | |
|---|---|---|---|
| Test agent | ng/mL | HUVEC | C3H10T1/2 |
| control | 0 | 100.0 | 100.0 |
| FGF-2 | 50 | 119.2 | 116.2 |
| Compound Example 4 | 50 | 135.8 | 170.4 |
| Compound Example 4 | 100 | 83.4 | 141.5 |

EXAMPLE 12

Cell growth was evaluated using Rat microvascular endothelial cells (RMEC) transformed by SV40 Large T-antigen (19,20) (gift from M. Goligorsky, Division of Nephrology and Hypertension, SUNY, Stony Brook). Cell growth was monitored using a commercially available kit (Promega Corporation, Madison, Wis.) based on a tetrazolium compound (3-(4,5-dimethylthiazol-2-yl)-5-(3-carboxymethoxyphenyl)-2-(4-sulfophenyl)-2H-tetrazolium, inner salt (MTS). Aliquots of $10^3$ RMEC cells were seeded into wells of 96-well plates and allowed to attach. The medium was replaced with one containing low serum plus Compound of Example 4. FGF-2 (50 ng/mL) was used as a reference material. After 3 days in culture, the relative cell number was monitored using MTS following the directions of the manufacturer. An increase in relative cell number was found for all concentrations tested between 1 and 200 ng/mL, as shown in Table 4:

TABLE 4

| ng/mL | Absorbance 490 nm | S.D. | % of control value |
|---|---|---|---|
| 0 | 0.47 | 0.04 | 100.0 |
| 1 | 0.58* | 0.05 | 121.5 |
| 10 | 0.61* | 0.05 | 128.2 |
| 20 | 0.63* | 0.03 | 133.4 |
| 50 | 0.60* | 0.08 | 125.6 |
| 100 | 0.71* | 0.04 | 149.6 |
| 200 | 0.66* | 0.05 | 138.6 |
| FGF-2 | 0.53* | 0.07 | 111.7 |

The asterisk indicates $p \leq 0.05$ determined using ANOVA followed by post hoc multiple comparisons versus the control group (Dunnett's Method). A similar response was obtained with C3H10T1/2 fibroblasts. Treatment of RMEC cells with Compound of Example 4 resulted in an increased secretion of gelatinase over a range of 0.5 to 50 ng/mL, as shown in Table 5. FGF-2, which was used as a positive control, also increased the secretion of gelatinase.

TABLE 5

| | absorbance 405 nm | | |
|---|---|---|---|
| | Mean | Std Dev | P vs control |
| 0 | 0.64 | 0.05 | — |
| 0.5 | 0.32 | 0.13 | 0.005 |
| 1 | 0.44 | 0.12 | 0.104 |
| 5 | 0.42 | 0.08 | 0.074 |
| 10 | 0.36 | 0.11 | 0.014 |
| 50 | 0.37 | 0.04 | 0.020 |

RMEC cells were grown in serum low medium and stimulated for 48 hours with Compound of Example 4. The medium was then removed and assayed for activity. In the assay the activity was inversely related to the enzyme concentration. Cultures treated with FGF-2 over a similar concentration range also induced gelatinase. Statistical significance was determined by ANOVA on ranks with subsequent post hoc analysis using multiple comparisons versus control group (Bonnferri t-test).

EXAMPLE 13

Figure 9:
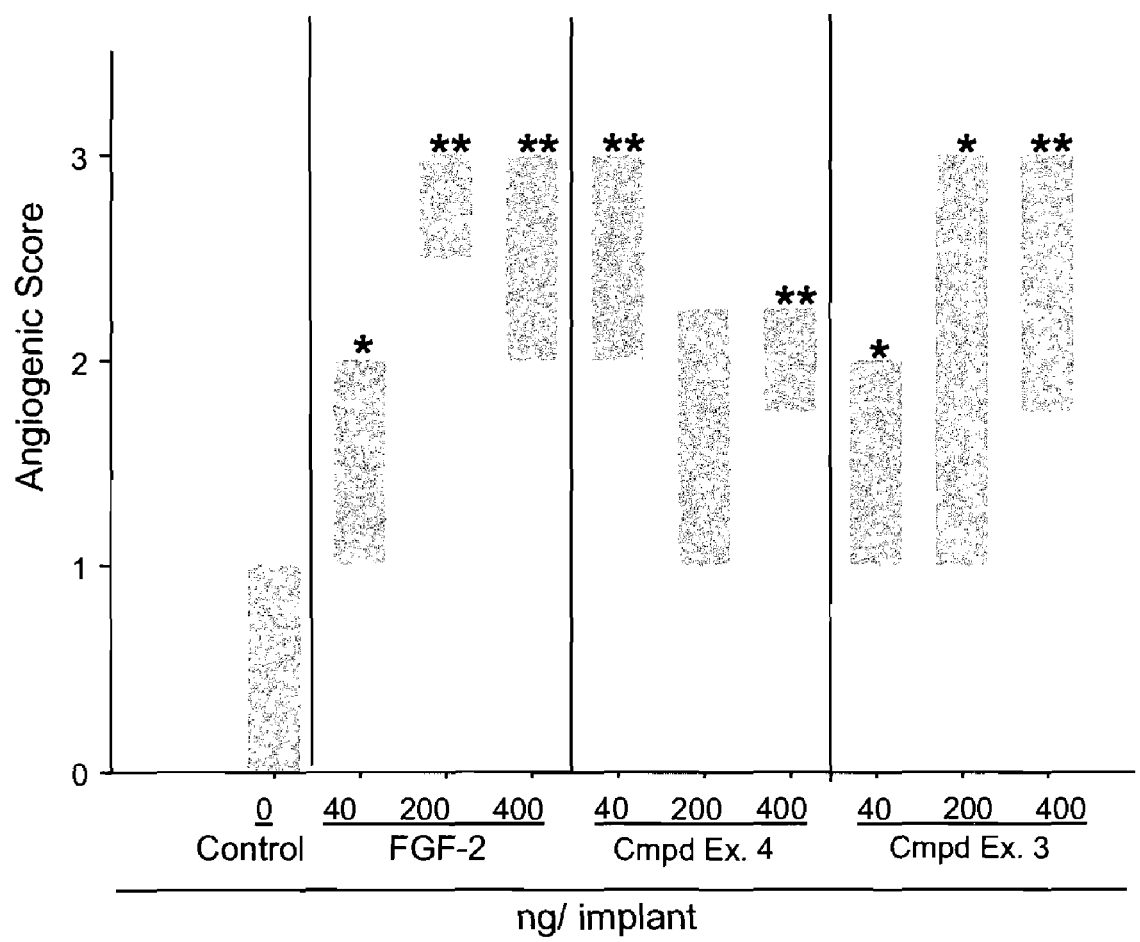
FIG. 9 is a plot of angiogenic scores assigned according to the following criteria: 0, no vessel; 1, few tiny vessels; 2, larger vessels with shallow penetration; and 3, several larger vessels with deep penetration. Compounds tested were FGF-2 and the Compounds of Example 3 and 4. The bar plot shows the 10th and 90th percentiles of the angiogenic score. Data were analyzed by use of the Mann-Whitney Rank Sum Test. (*, p<0.05; **, p<0.01) according to one embodiment of the present invention.
Figure 10:
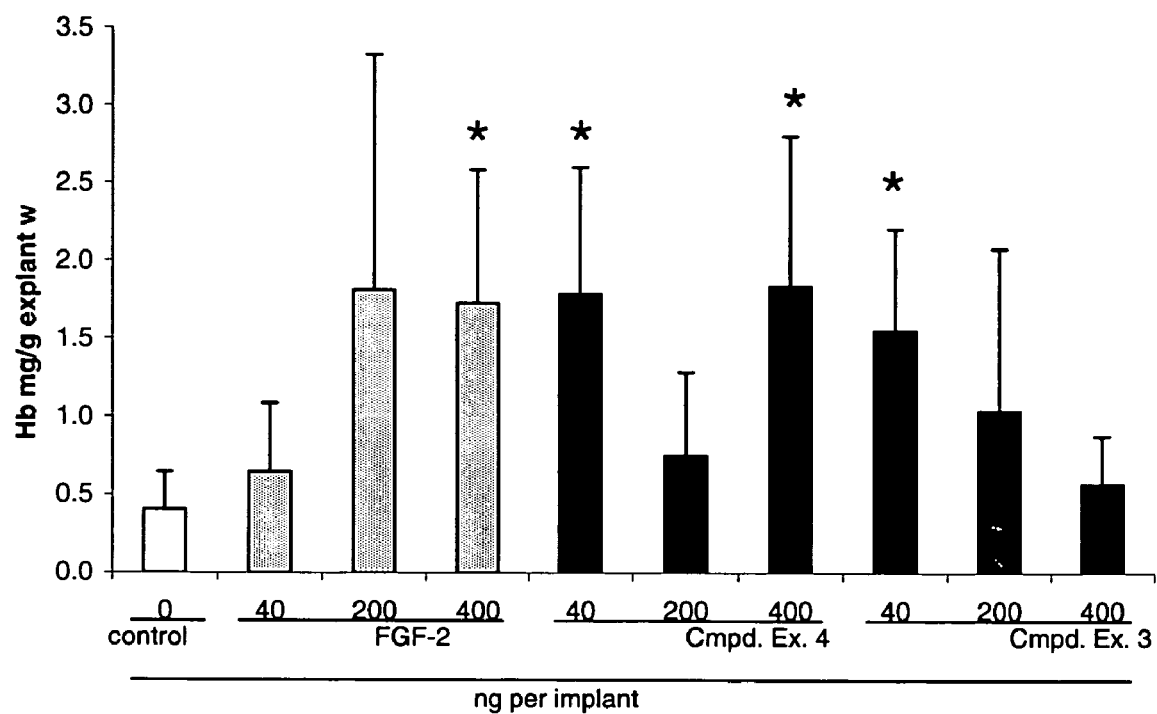
FIG. 10 is a plot according to one embodiment of the present invention of hemoglobin (Hb) content of Matrigel plugs. Hemoglobin was extracted from the plugs and converted to hemiglobin-ferricyanate with Drabkin's reagent with subsequent monitoring at 550 nm using bovine hemoglobin as standard. Data is reported as the average of at least 5 determinations±S.D. Statistical analysis was performed by ANOVA with a post-hoc Tukey test for each group. Asterisks indicate p<0.05 compared to the controls.

An in vivo angiogenesis model was used with implant of Matrigel with and without additives (22). In the experiments, C57BL/6 mice were used, with aliquots of 0.4 ml of Matrigel injected subcutaneously, large enough to form a plug that could be consistently visualized and was small enough to be practical. Growth factor reduced Matrigel at 4° C. (liquid state) was mixed with 0.1 or 1.0 μg/mL of basic fibroblast growth factor (FGF-2; R&D Systems, Minneapolis, Minn.), Compound of Example 4 or Compound of Example 3. Aliquots of 0.4 mL of Matrigel with or without additives were injected subcutaneously in the right paraspinal space and 0.4 mL without additives was injected subcutaneously in the left paraspinal space as control. After 5 days the animals were euthanized and the Matrigel plug dissected away from the host tissue, photographed, an angiogenic score assigned (23), the tissue frozen in sealed tubes, and weights of the explants determined. Two observers reviewed the photographs of each plug, which were not identified, and graded by consensus the angiogenic response. The angiogenic score was determined on a scale of 0-3. Plugs with no blood vessels were assigned a score of 0, those with few tiny peripheral vessels were assigned 1, and those with larger vessels with shallow penetration scored 2, and those with several large vessels with deep penetration were scored 3. For hemoglobin determination, the tissue was extracted for approximately 1 hour by adding 150 µL of 0.5% Triton X 100 and later 50 µL of Dispase with periodic vortexing and sonication. An aliquot of 60 µL of the extract was removed for analysis. In the assay, hemoglobin (HB) was converted to hemoglobin-ferricyanate with following 5-minute incubation with 200 µL of Drabkin's reagent (SigmaAldrich, St. Louis, Mo.) and monitored with a microplate reader at 525 nm using bovine hemoglobin as standard. Compound of Example 4 caused angiogenesis in vivo as monitored using the Matrigel plug assay, as shown in FIG. 9, as did FGF-2, which was used as a system control. Angiogenic response as monitored by visual scoring indicated a significant response when Compound of Example 4 was used at 40 and 400 ng/mL, a response that was verified by histological examination. A quantitative assessment of the hemoglobin content of the plugs also indicated a significantly higher amount of hemoglobin in plugs that were implanted with both Compound of Example 3 or 4 when compared to controls, as shown in FIG. 10. In control experiments, Ahx-Ahx-AhxRKRKLERIAR-NH$_2$ (SEQ ID NO:27), the heparin binding domain (minus the receptor targeting domain), did not stimulate angiogenesis as determined by either visual scoring or by quantization of hemoglobin. Data in FIG. 10 is the average of at least 5 determinations±S.D. Statistical significance was determined following Turkey test with ad hoc determination of significance assumed to be greater than 0.05. Statistical analysis was performed by ANOVA with a post-hoc Tukey test for each group. Asterisks indicate p<0.05 compared to the controls.

EXAMPLE 14

Figure 11:
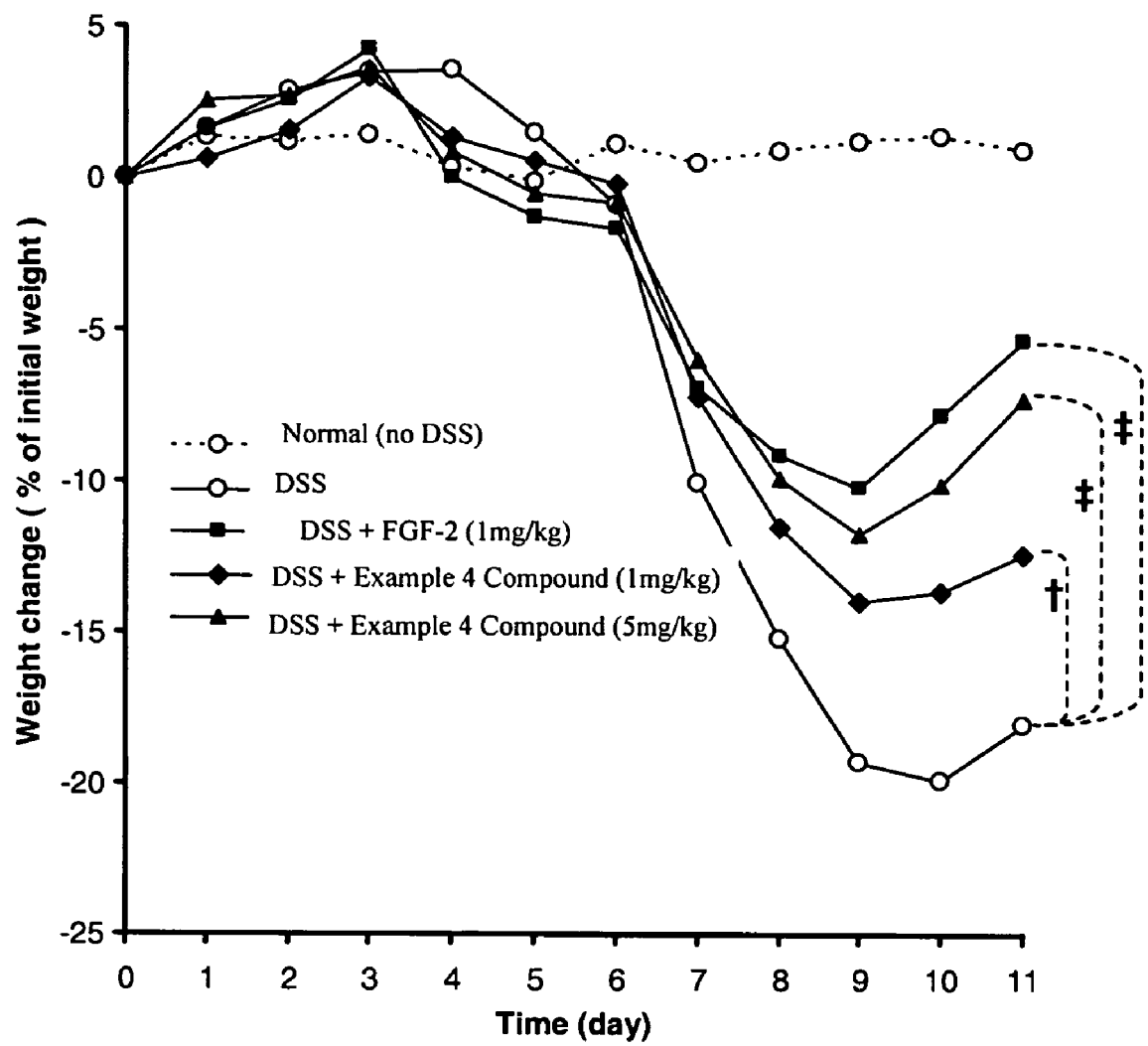
FIG. 11 illustrates a plot according to one embodiment of the present invention of weight change in animals with and without induced ulcerative colitis in the presence and absence of an FGF analog administered perenterally.
Figure 12:
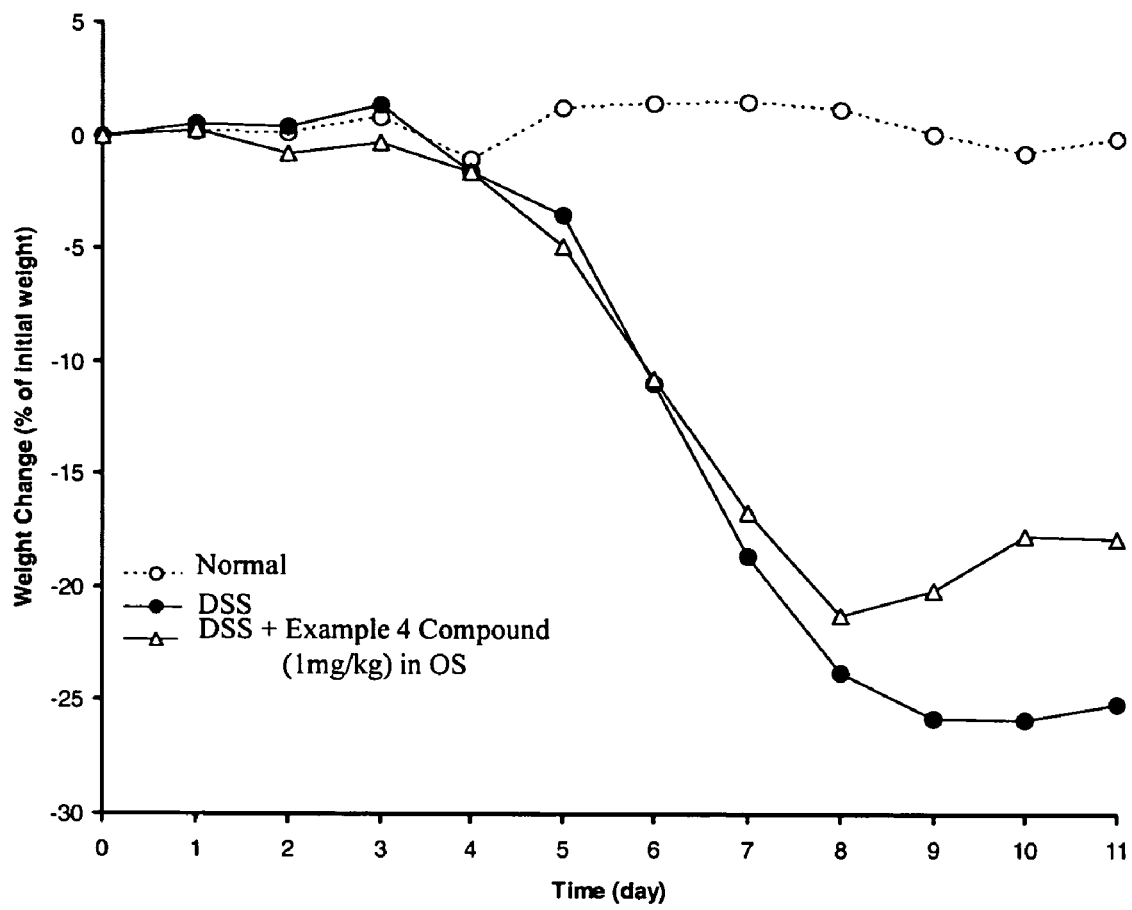
FIG. 12 illustrates a plot according to one embodiment of the present invention of weight change in animals with and without induced ulcerative colitis in the presence and absence of an FGF analog administered perenterally.

According to one example of a perenteral use, the compound in Example 4 was used to ameliorate the symptoms of experimental ulcerative colitis. C57BL/6 mice (n=10/group) were given 3% dextran sulfate (DSS) in their drinking water for 5 days, then switched to regular drinking water. Normal control mice received only regular drinking water. Starting at day 3, the experimental animals received intra-peritoneal injections of saline containing the Compound of Example 4 (1- or 5 mg/kg) or rhFGF-2 (1 mg/kg) once a day for 5 days. Normal and untreated DSS-induced mice received saline injections. Body weight was measured daily throughout for a total of 11 days and is presented in FIG. 12 as average weight loss. Statistical significance was determined following a one-day, repeated-measures ANOVA with post hoc testing, and in FIG. 11 where ‡ indicates a statistical significance with p greater than 0.05, and † indicates a trend to significance with p=0.12. In colitis mice with no therapy, body weights decreased gradually from day 4 to day 9 and the loss of body weight has not regained at the end of the experiment (FIG. 12). The colons in these animals were shortened and had clear signs of inflammation including thickening of the bowel and increased vascularization. Histological evaluation showed a loss of epithelium and crypt morphology, depletion of goblet cells, necrosis, ulceration and transmural infiltration of granulocytes. In contrast, colitis animals treated with the Compound of Example 4 had slower rates of weight loss during the study. Moreover, the Compound of Example 4 promoted the recovery of weight loss compared to untreated mice once DSS treatment was stopped. Colons of these animals exhibited milder signs of inflammation including less shortening and thickening. Histologically, colons of mice treated with the Compound of Example 4 exhibited morphologies more reminiscent of normal tissue architecture with an intact epithelium and complete crypts Inflammation, while present, was mild and considerably less extensive than in untreated animals. The return to more normal morphology was especially noticeable in animals receiving doses of 5 mg/kg. Animals treated with hrFGF-2, the reference treatment, also had increased body weights and histologically were similar to those treated with the Compound of Example 4 and 5 mg/kg. Collectively, the results demonstrate therapeutic effects of the Compound of Example 4 in experimental ulcerative colitis.

EXAMPLE 15

As an example of an oral route of administration, the compound in Example 4 was given orally to mice with experimentally induced ulcerative colitis. To induce ulcerative colitis, C57BL/6 mice were given 3% dextran sulfate (DSS) in their drinking water for 4 days then switched to regular drinking water. Normal control mice received regular drinking water throughout the experiment. Starting at day 3, animal received 40 ul of an aqueous solution of the Compound of Example 4 (1 mg/kg) plus a 2 molar equivalent of sucrose octasulfate once a day for 5 consecutive days. Both normal and untreated DSS-induced mice received an aqueous solution without the Compound of Example 4. Body weight was measured daily throughout the experiment which lasted a total of 11 days including the DSS treatment. Animals receiving the Compound of Example 4 had a significantly increase (P<0.005) in total body weight.

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover all such modifications and equivalents. The entire disclosures of all references, applications, patents, and publications cited above are hereby incorporated by reference.

What is claimed is:

1. A fibroblast growth factor heparin-binding analog of formula I:

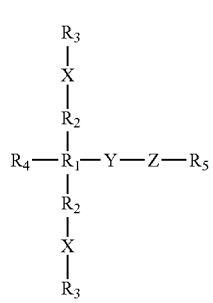

wherein:

X comprises a sequence selected from SEQ ID NO 7, SEQ ID NO 25 or SEQ ID NO 26;

$R_1$ is either a single trifunctional amino acid residue covalently bonded to each X or is a dipeptide of the formula $AA_1$-$AA_2$ wherein $AA_1$-$AA_2$ are each a trifunctional amino acid;

$R_2$ is 0;

Each $R_3$ is hydrogen (H) such that the terminal group is $NH_2$, or is an acyl group with a linear or branched $C_1$ to $C_{17}$ alkyl, aryl, heteroaryl, alkene, alkenyl or aralkyl chain including an N-terminus $NH_2$, $NH_3^+$, or NH group or a corresponding acylated derivative;

$R_4$ is present as $NH_2$ or H;

$R_5$ is OH, $NH_2$, or an acyl group with a linear or branched $C_1$ to $C_{17}$ alkyl, aryl, heteroaryl, alkene, alkenyl or aralkyl chain;

Y is a linker comprising Ahx-Ahx-Ahx; and

Z is selected from SEQ ID NO 2 or SEQ ID NO 5.

2. The compound of claim 1 wherein X and Z are synthetic peptide chains.

3. The compound of claim 1 wherein the compound of claim 1 has an avidity for heparin such that the compound of formula I binds heparin in 0.15 M NaCl, but is eluted by 1 M NaCl.

4. A pharmaceutical composition comprising the compound of claim 1 or a pharmaceutically acceptable salt thereof and a pharmaceutical carrier.

5. A medical device comprising the compound of claim 1 or a pharmaceutically acceptable salt thereof.

6. The analog of claim 1 wherein the structure is: H-K(H-YRSRKYSSWYVALKR)-K(H-YRSRKYSSWYVALKR)-Ahx-Ahx-Ahx-RKRKLERIAR-NH$_2$ wherein YRSRKYSSWYVALKR (SEQ ID NO: 7) is X and RKRKLERIAR (SEQ ID NO: 2) is Z.

7. The analog of claim 1 wherein the structure is: H-K(H-RKLAVYWSSYKRSRY)-K(H-RKLAVYWSSYKRSRY)-Ahx-Ahx-Ahx-RKRKLERIAR-NH$_2$ wherein RKLAVYWSSYKRSRY (SEQ ID NO: 26) is X and RKRKLERIAR (SEQ ID NO: 2) is Z.

8. The analog of claim 1 wherein the structure is: H-K(H-AESGDDYCVLVFTDSAWTKICDWSHFRN)-K(H-AESGDDYCVLVFTDSAWTKICDWSHFRN)-Ahx-Ahx-Ahx-RKRKLERIAR-NH$_2$ wherein AESGDDYCVLVFTDSAWTKICDWSHFRN (SEQ ID NO: 25) is X and RKRKLERIAR (SEQ ID NO: 2) is Z.

9. A fibroblast growth factor heparin-binding analog of formula I:

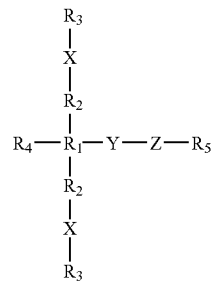

wherein:
X is SEQ ID NO 7;
$R_1$ is a single trifunctional amino acid residue covalently bonded to each X when $R_2$ is 0;
$R_2$ is 0 peptide bonds;
Each $R_3$ is hydrogen (H) such that the terminal group is $NH_2$, or is an acyl group with a linear or branched $C_1$ to $C_{17}$ alkyl, aryl, heteroaryl, alkene, alkenyl or aralkyl chain including an N-terminus $NH_2$, $NH_3^+$, or NH group or a corresponding acylated derivative;
$R_4$ is not present if $R_1$ is a single trifunctional amino acid residue;
$R_5$ is OH, $NH_2$, or a linear or branched $C_1$ to $C_{17}$ alkyl, aryl, heteroaryl, alkene, alkenyl or aralkyl chain;
Y is a linker Ahx-Ahx-Ahx; and
Z is SEQ ID NO 5.

10. The analog of claim 9 wherein the structure is: H-YRSRKYSSWYVALKRK(H-YRSRKYSSWYVALKR)-Ahx-Ahx-Ahx-RKRLDRIAR-NH$_2$ wherein YRSRKYSSWYVALKRK (SEQ ID NO: 7) is X and RKRLDRIAR (SEQ ID NO: 5) is Z.

* * * * *

UNITED STATES PATENT AND TRADEMARK OFFICE
CERTIFICATE OF CORRECTION

PATENT NO. : 8,227,411 B2
APPLICATION NO. : 11/361565
DATED : July 24, 2012
INVENTOR(S) : Zamora et al.

It is certified that error appears in the above-identified patent and that said Letters Patent is hereby corrected as shown below:

On the title page, item [73] should read: BIOSURFACE ENGINEERING TECHNOLOGIES, INC., Rockville, MD (US); BROOKHAVEN SCIENCE ASSOCIATES, Upton, NY (US)

Signed and Sealed this
Ninth Day of September, 2014

Michelle K. Lee
*Deputy Director of the United States Patent and Trademark Office*